United States Patent
Vejborg et al.

(10) Patent No.: US 11,414,652 B2
(45) Date of Patent: *Aug. 16, 2022

(54) CLEANING COMPOSITIONS COMPRISING ENZYMES

(71) Applicant: NOVOZYMES A/S, Bagsvaerd (DK)

(72) Inventors: Rebecca Munk Vejborg, Alleroed (DK); Klaus Gori, Dyssegaard (DK); Lilian Eva Tang Baltsen, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/306,048

(22) PCT Filed: Jun. 2, 2017

(86) PCT No.: PCT/EP2017/063489
§ 371 (c)(1),
(2) Date: Nov. 30, 2018

(87) PCT Pub. No.: WO2017/207770
PCT Pub. Date: Dec. 7, 2017

(65) Prior Publication Data
US 2019/0161707 A1    May 30, 2019

(30) Foreign Application Priority Data

Jun. 3, 2016 (DK) ............................ PA 2016 00328

(51) Int. Cl.
| | |
|---|---|
| *C12N 9/26* | (2006.01) |
| *C12N 9/16* | (2006.01) |
| *C11D 3/386* | (2006.01) |
| *C12N 9/24* | (2006.01) |
| *C12N 9/22* | (2006.01) |

(52) U.S. Cl.
CPC ........ *C12N 9/2402* (2013.01); *C11D 3/38618* (2013.01); *C11D 3/38627* (2013.01); *C11D 3/38636* (2013.01); *C11D 3/38645* (2013.01); *C11D 3/38654* (2013.01); *C11D 3/38663* (2013.01); *C12N 9/22* (2013.01)

(58) Field of Classification Search
CPC .... C12N 9/2402; C12N 9/22; C11D 3/38636; C11D 3/386
See application file for complete search history.

(56) References Cited

U.S. PATENT DOCUMENTS

| | | | |
|---|---|---|---|
| 6,468,955 B1 | 10/2002 | Smets | |
| 10,131,863 B2 * | 11/2018 | Gori | ............... C11D 3/38636 |
| 10,479,981 B2 * | 11/2019 | Oestergaard | ... C12Y 301/21001 |
| 10,626,354 B2 * | 4/2020 | Ooehlenschlaeger | .................... C12Y 302/01052 |
| 2012/0258089 A1 | 10/2012 | Madhyastha | |

FOREIGN PATENT DOCUMENTS

| | | |
|---|---|---|
| WO | 98/50512 A1 | 11/1998 |
| WO | 99/057157 A1 | 11/1999 |
| WO | 2004/061117 A2 | 11/2004 |
| WO | 2009/061380 A2 | 5/2009 |
| WO | 2009/121183 A1 | 10/2009 |
| WO | 2014/087011 A1 | 6/2014 |
| WO | 2015/155350 A1 | 10/2015 |
| WO | 2015/181286 A1 | 12/2015 |

OTHER PUBLICATIONS

Wang. A0A075LPR4. UniProtKB Database. 2014.*
Kaplan et al., 2009, International journal of artificial organs 32(9), 545-554.
Kaplan et al., 2014, Methods Mol Biol 1147,203-213.

* cited by examiner

*Primary Examiner* — Yong D Pak
(74) *Attorney, Agent, or Firm* — Yoshimi Barron

(57) ABSTRACT

The present invention relates to compositions, methods and use of a mixture of enzymes having DNase activity and an enzyme having hexosaminidase activity.

15 Claims, No Drawings
Specification includes a Sequence Listing.

SEQUENCE LISTING

<160> NUMBER OF SEQ ID NOS: 20

<210> SEQ ID NO 1
<211> LENGTH: 732
<212> TYPE: DNA
<213> ORGANISM: Aspergillus oryzae

<400> SEQUENCE: 1

```
atgcagctta ctaagtccct cctggtattc gcgctttaca tgtttggcac tcagcacgtt      60
ctagctgtgc ctgtcaatcc cgagcctgat gctacgagcg tcgaaaatgt tgcccttaaa     120
acaggcagcg gtgatagcca gagcgatccc atcaaggcgg acttggaggt caaaggccaa     180
agtgctttgc ctttcgacgt cgactgctgg gctatcctgt gcaagggcgc cccgaatgtc     240
ctgcagcgcg tgaatgaaaa gacgaaaaat agtaatcgcg atcggagcgg tgcgaacaaa     300
gggcctttca agatcctca gaaatggggc atcaaagccc ttccacctaa gaatccatcc      360
tggagcgcac aagacttcaa atcacccgaa gaatacgcat ttgcgtcttc ccttcaaggc     420
ggaaccaatg ccatcctagc gcccgtcaac ctcgcttctc agaactccca aggcggcgtc     480
ttgaacggtt tctactcggc gaacaaagta gcacaatttg atcctagcaa gccccaacag     540
acaaagggaa catggtttca gatcactaag ttcacaggtg cagctggtcc ttactgcaag     600
gctctgggga gtaatgataa gagtgtgtgc gataagaaca agaatattgc aggggactgg     660
ggcttcgacc cggcgaaatg gcatatcag tatgatgaga agaataacaa gttcaactat      720
gttggtaagt aa                                                          732
```

<210> SEQ ID NO 2
<211> LENGTH: 221
<212> TYPE: PRT
<213> ORGANISM: Aspergillus oryzae

<400> SEQUENCE: 2

```
Val Pro Val Asn Pro Glu Pro Asp Ala Thr Ser Val Glu Asn Val Ala
1               5                   10                  15
Leu Lys Thr Gly Ser Gly Asp Ser Gln Ser Asp Pro Ile Lys Ala Asp
            20                  25                  30
Leu Glu Val Lys Gly Gln Ser Ala Leu Pro Phe Asp Val Asp Cys Trp
        35                  40                  45
Ala Ile Leu Cys Lys Gly Ala Pro Asn Val Leu Gln Arg Val Asn Glu
    50                  55                  60
Lys Thr Lys Asn Ser Asn Arg Asp Arg Ser Gly Ala Asn Lys Gly Pro
65                  70                  75                  80
Phe Lys Asp Pro Gln Lys Trp Gly Ile Lys Ala Leu Pro Pro Lys Asn
                85                  90                  95
Pro Ser Trp Ser Ala Gln Asp Phe Lys Ser Pro Glu Glu Tyr Ala Phe
            100                 105                 110
Ala Ser Ser Leu Gln Gly Gly Thr Asn Ala Ile Leu Ala Pro Val Asn
        115                 120                 125
Leu Ala Ser Gln Asn Ser Gln Gly Gly Val Leu Asn Gly Phe Tyr Ser
    130                 135                 140
Ala Asn Lys Val Ala Gln Phe Asp Pro Ser Lys Pro Gln Gln Thr Lys
145                 150                 155                 160
Gly Thr Trp Phe Gln Ile Thr Lys Phe Thr Gly Ala Ala Gly Pro Tyr
                165                 170                 175
Cys Lys Ala Leu Gly Ser Asn Asp Lys Ser Val Cys Asp Lys Asn Lys
            180                 185                 190
```

```
Asn Ile Ala Gly Asp Trp Gly Phe Asp Pro Ala Lys Trp Ala Tyr Gln
            195                 200                 205

Tyr Asp Glu Lys Asn Asn Lys Phe Asn Tyr Val Gly Lys
210                 215                 220

<210> SEQ ID NO 3
<211> LENGTH: 351
<212> TYPE: PRT
<213> ORGANISM: Actinobacillus pleuropneumoniae

<400> SEQUENCE: 3

Met Asp Leu Pro Lys Lys Glu Ser Gly Leu Thr Leu Asp Ile Ala Arg
1               5                   10                  15

Arg Phe Tyr Thr Val Asp Thr Ile Lys Gln Phe Ile Asp Thr Ile His
            20                  25                  30

Gln Ala Gly Gly Thr Phe Leu His Leu His Phe Ser Asp His Glu Asn
        35                  40                  45

Tyr Ala Leu Glu Ser Ser Tyr Leu Glu Gln Arg Glu Glu Asn Ala Thr
    50                  55                  60

Glu Lys Asn Gly Thr Tyr Phe Asn Pro Lys Thr Asn Lys Pro Phe Leu
65                  70                  75                  80

Thr Tyr Lys Gln Leu Asn Glu Ile Ile Tyr Tyr Ala Lys Glu Arg Asn
                85                  90                  95

Ile Glu Ile Val Pro Glu Val Asp Ser Pro Asn His Met Thr Ala Ile
            100                 105                 110

Phe Asp Leu Leu Thr Leu Lys His Gly Lys Glu Tyr Val Lys Gly Leu
        115                 120                 125

Lys Ser Pro Tyr Ile Ala Glu Glu Ile Asp Ile Asn Asn Pro Glu Ala
    130                 135                 140

Val Glu Val Ile Lys Thr Leu Ile Gly Glu Val Ile Tyr Ile Phe Gly
145                 150                 155                 160

His Ser Ser Arg His Phe His Ile Gly Gly Asp Glu Phe Ser Tyr Ala
                165                 170                 175

Val Glu Asn Asn His Glu Phe Ile Arg Tyr Val Asn Thr Leu Asn Asp
            180                 185                 190

Phe Ile Asn Ser Lys Gly Leu Ile Thr Arg Val Trp Asn Asp Gly Leu
        195                 200                 205

Ile Lys Asn Asn Leu Ser Glu Leu Asn Lys Asn Ile Glu Ile Thr Tyr
    210                 215                 220

Trp Ser Tyr Asp Gly Asp Ala Gln Ala Lys Glu Asp Ile Gln Tyr Arg
225                 230                 235                 240

Arg Glu Ile Arg Ala Asp Leu Pro Glu Leu Leu Ala Asn Gly Phe Lys
                245                 250                 255

Val Leu Asn Tyr Asn Ser Tyr Tyr Leu Tyr Phe Val Pro Lys Ser Gly
            260                 265                 270

Ser Asn Ile His Asn Asp Gly Lys Tyr Ala Ala Glu Asp Val Leu Asn
        275                 280                 285

Asn Trp Thr Leu Gly Lys Trp Asp Gly Lys Asn Ser Ser Asn His Val
    290                 295                 300

Gln Asn Thr Gln Asn Ile Gly Ser Ser Leu Ser Ile Trp Gly Glu
305                 310                 315                 320

Arg Ser Ser Ala Leu Asn Glu Gln Thr Ile Gln Gln Ala Ser Lys Asn
                325                 330                 335

Leu Leu Lys Ala Val Ile Gln Lys Thr Asn Asp Pro Lys Ser His
```

<210> SEQ ID NO 4
<211> LENGTH: 359
<212> TYPE: PRT
<213> ORGANISM: Aggregatibacter actinomycetemcomitans

<400> SEQUENCE: 4

```
Cys Val Lys Gly Asn Ser Ile His Pro Gln Lys Thr Ser Thr Lys Gln
1               5                   10                  15

Thr Gly Leu Met Leu Asp Ile Ala Arg His Phe Tyr Ser Pro Glu Val
            20                  25                  30

Ile Lys Ser Phe Ile Asp Thr Ile Ser Leu Ser Gly Gly Asn Phe Leu
        35                  40                  45

His Leu His Phe Ser Asp His Glu Asn Tyr Ala Ile Glu Ser His Leu
    50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Ile Lys Tyr Leu Gln Gly Leu Lys Ser Arg Gln Val Asp
    130                 135                 140

Asp Glu Ile Asp Ile Thr Asn Ala Asp Ser Ile Ala Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Ser Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Ala Asn Gly Asp Glu
        355
```

<210> SEQ ID NO 5
<211> LENGTH: 346
<212> TYPE: PRT
<213> ORGANISM: Haemophilus sputorum

<400> SEQUENCE: 5

Gln Asn Ser Thr Lys Gln Ser Gly Leu Met Leu Asp Ile Ser Arg Arg
1               5                   10                  15

Phe Tyr Ser Val Glu Thr Ile Lys Gln Phe Ile Asp Asp Ile Ala Gln
            20                  25                  30

Ala Asn Gly Thr Phe Leu His Leu His Phe Ala Asp His Glu Asn Tyr
        35                  40                  45

Ala Leu Glu Ser Thr Phe Leu Asn Gln Arg Ala Glu Asn Ala Ile Val
    50                  55                  60

Gln Asn Gly Ile Tyr Ile Asn Pro Lys Thr Asn Lys Pro Phe Leu Thr
65                  70                  75                  80

Tyr Glu Gln Ile Asp Gln Ile Ile Arg Tyr Ala Gln Glu Lys Gln Ile
                85                  90                  95

Glu Leu Ile Pro Glu Val Asp Ser Pro Ala His Ile Lys Gly Ile Leu
            100                 105                 110

Thr Leu Leu Arg Leu Glu Lys Gly Glu Asp Tyr Val Asn Gln Ile Ala
        115                 120                 125

Leu Asn Gln Asp Glu Leu Asn Leu Asp Ser Pro Glu Ser Leu Thr Met
    130                 135                 140

Met Lys Thr Leu Val Asp Glu Val Cys Tyr Ile Phe Gly Tyr Ser Ala
145                 150                 155                 160

Gln His Phe His Ile Gly Gly Asp Glu Phe Asn Tyr Ala Ser Asn Phe
                165                 170                 175

Ile Arg Tyr Val Asn Ala Leu Asn Gln His Ile Asn Gln Lys Gly Leu
            180                 185                 190

Ile Thr Arg Met Trp Asn Asp Gly Leu Leu Gln Gln Asn Ile Asp Glu
        195                 200                 205

Leu Asp Lys Asn Ile Glu Ile Thr Tyr Trp Ser Phe Asp Gly Asp Ala
    210                 215                 220

Gln Glu Lys Asn Asp Ile Val Glu Arg Arg Ala Thr Arg Ile Ser Leu
225                 230                 235                 240

Pro Thr Leu Leu Asp Lys Gly Phe Lys Ala Leu Asn Tyr Asn Ser Tyr
                245                 250                 255

Tyr Leu Tyr Phe Ile Pro Lys Asp Asn Gly Asn Ile Ala Thr Asp Ala
            260                 265                 270

Lys Phe Ala Leu Asn Asp Leu Lys Gln Asn Trp Gln Leu Leu Arg Trp
        275                 280                 285

Asp Gly Asn Tyr Glu Thr Gln Pro Ile Gln Gln Ala Glu Asn Leu Ile
    290                 295                 300

Gly Ala Ala Phe Ser Ile Trp Gly Glu His Ala Gly Lys Leu Ser Asp
305                 310                 315                 320

Asp Val Ile His Gln Ala Thr Ser Pro Leu Ile Gln Ala Thr Ile Ile
                325                 330                 335

Gln Thr Asn Ala Lys Thr Thr Gly Pro Asn
            340                 345

<210> SEQ ID NO 6
<211> LENGTH: 352
<212> TYPE: PRT
<213> ORGANISM: Actinobacillus suis

<400> SEQUENCE: 6

```
Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Ser Glu Ala Asn Ala
    50                  55                  60

Ile Val Lys Asp Gly Thr Tyr Tyr Asn Pro Lys Thr Asn Lys Pro Phe
65                  70                  75                  80

Leu Thr Tyr Lys Gln Ile His Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Gly Lys Asp Tyr Val Lys Lys
        115                 120                 125

Leu Lys Ser Lys Met Asn Asp Glu Glu Ile Asp Ile Thr Asn Pro Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Asp Glu Phe Gly Tyr
                165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Ala Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys Tyr Ala Thr Glu Asp Val Leu
        275                 280                 285

Asn Asn Trp Lys Leu Gly Leu Trp Asp Gly Gln Asn Lys Glu Asn Met
    290                 295                 300

Val Glu Asn Thr Lys Asn Ile Ile Gly Ser Ser Leu Ser Ile Trp Gly
305                 310                 315                 320

Glu Arg Ser Gly Ser Leu Ser Ser Glu Val Ile Glu Glu Ser Thr Gln
                325                 330                 335

Asp Leu Leu Lys Ala Val Ile Gln Lys Thr Asn Asp Pro Lys Ser His
            340                 345                 350
```

<210> SEQ ID NO 7
<211> LENGTH: 352
<212> TYPE: PRT
<213> ORGANISM: Actinobacillus capsulatus

<400> SEQUENCE: 7

```
Met Asn His Ser Gln Ile Lys Glu Ala Gly Leu Thr Leu Asp Ile Ala
1               5                   10                  15
```

```
Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Leu Glu Ala Asn Ala
 50                  55                  60

Ile Val Lys Asp Gly Thr Tyr Tyr Asn Pro Thr Thr Asn Lys Pro Phe
 65                  70                  75                  80

Leu Thr Tyr Lys Gln Ile Asn Asp Ile Ile Tyr Tyr Ala Lys Ser Lys
                 85                  90                  95

Asn Ile Glu Leu Val Pro Glu Val Asp Thr Pro Asn His Met Thr Ala
                100                 105                 110

Ile Phe Arg Leu Leu Glu Ala Lys His Ser Lys Asp Tyr Val Lys Arg
            115                 120                 125

Leu Lys Ser Lys Met Asn Asp Glu Glu Ile Asp Ile Thr Asn Leu Glu
130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Thr Tyr Val Asn Thr Leu Asn
                180                 185                 190

Gln Phe Ile Asn Asn Lys Gly Lys Ile Thr Arg Ile Trp Asn Asp Gly
            195                 200                 205

Leu Ile Lys Asn Asn Leu Asn Gln Leu Asn Lys Asn Val Glu Ile Thr
            210                 215                 220

Tyr Trp Ser Tyr Asp Gly Asp Ala Gln Glu Ser Gln Asp Ile Ala Glu
225                 230                 235                 240

Arg Arg Lys Ile Arg Val Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys His Ala Thr Glu Asp Val Leu
            275                 280                 285

Lys Asn Trp Lys Leu Gly Leu Trp Asp Gly Gln Asn Lys Glu Asn Ile
290                 295                 300

Val Glu Asn Thr Lys Asn Ile Ile Gly Ser Ser Leu Ser Ile Trp Gly
305                 310                 315                 320

Glu His Ser Gly Ser Leu Ser Ser Ala Val Ile Glu Glu Ser Thr Gln
                325                 330                 335

Glu Leu Leu Lys Ala Val Ile Gln Lys Thr Asn Asp Pro Lys Ser His
            340                 345                 350

<210> SEQ ID NO 8
<211> LENGTH: 352
<212> TYPE: PRT
<213> ORGANISM: Actinobacillus equuli subsp. equuli

<400> SEQUENCE: 8

Met Asn His Ser Gln Ile Lys Glu Ala Gly Leu Thr Leu Asp Ile Ala
 1               5                  10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
```

```
            35                  40                  45
Asn Tyr Ala Leu Glu Ser Ser Tyr Leu Asp Gln Ser Glu Glu Asn Ala
             50                  55                  60

Ile Val Lys Asp Gly Thr Tyr Asn Pro Lys Thr Asn Lys Pro Phe
 65                  70                  75                  80

Leu Thr Tyr Lys Gln Ile Asp Asp Ile Tyr Tyr Ala Lys Ser Lys
                 85                  90                  95

Asn Ile Glu Leu Val Pro Glu Val Asp Thr Pro Asn His Met Thr Ala
            100                 105                 110

Ile Phe Asn Leu Leu Glu Ile Lys His Gly Glu Ala Tyr Val Lys Asn
            115                 120                 125

Leu Lys Ser Lys Met Asn Asp Glu Glu Ile Asp Ile Thr Asn Pro Glu
            130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly
            195                 200                 205

Leu Ile Lys Asn Asn Leu Asn Gln Leu Asn Lys Asn Val Glu Ile Thr
210                 215                 220

Tyr Trp Ser Tyr Asp Gly Asp Ala Gln Lys Ser Gln Asp Ile Ala Glu
225                 230                 235                 240

Arg Arg Lys Ile Arg Ala Asp Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys Tyr Ala Thr Glu Asp Val Leu
            275                 280                 285

Asn Asn Trp Lys Leu Gly Leu Trp Asp Gly Asn Lys Glu Asn Glu
290                 295                 300

Val Lys Asn Thr Lys Asn Ile Ile Gly Ser Ser Leu Ser Ile Trp Gly
305                 310                 315                 320

Glu Arg Ser Gly Ser Leu Ser Ser Glu Val Ile Glu Glu Ser Thr Gln
                325                 330                 335

Asp Leu Leu Lys Ala Val Ile Gln Lys Thr Asn Asp Pro Lys Ser His
            340                 345                 350
```

<210> SEQ ID NO 9
<211> LENGTH: 359
<212> TYPE: PRT
<213> ORGANISM: Aggregatibacter actinomycetemcomitans

<400> SEQUENCE: 9

```
Cys Val Lys Gly Asn Ser Ile Tyr Pro Gln Lys Ile Ser Thr Lys Gln
  1               5                  10                  15

Thr Gly Leu Met Leu Asp Ile Ala Arg His Phe Tyr Ser Pro Glu Val
             20                  25                  30

Ile Lys Ser Phe Ile Asp Thr Ile Ser Leu Ser Gly Gly Asn Phe Leu
             35                  40                  45

His Leu His Phe Ser Asp His Glu Asn Tyr Ala Ile Glu Ser His Leu
 50                  55                  60
```

```
Leu Asn Gln Arg Ala Glu Asn Ala Val Gln Gly Lys Asp Gly Ile Tyr
 65                  70                  75                  80

Ile Asn Pro Tyr Thr Gly Lys Pro Phe Leu Ser Tyr Arg Gln Leu Asp
                 85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
    130                 135                 140

Asp Glu Ile Asp Ile Thr Asn Ala Asp Ser Ile Ala Phe Met Gln Ser
145                 150                 155                 160

Leu Met Asn Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Ser Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
        355

<210> SEQ ID NO 10
<211> LENGTH: 359
<212> TYPE: PRT
<213> ORGANISM: Aggregatibacter actinomycetemcomitans

<400> SEQUENCE: 10

Cys Val Lys Gly Asn Ser Ile Tyr Pro Gln Lys Thr Ser Thr Lys Gln
  1               5                  10                  15

Thr Gly Leu Met Leu Asp Ile Ala Arg His Phe Tyr Ser Pro Glu Val
                 20                  25                  30

Ile Lys Ser Phe Ile Asp Thr Ile Ser Leu Ser Gly Gly Asn Phe Leu
             35                  40                  45

His Leu His Phe Ser Asp His Glu Asn Tyr Ala Ile Glu Ser His Leu
         50                  55                  60

Leu Asn Gln Arg Ala Glu Asn Ala Val Gln Gly Lys Asp Gly Ile Tyr
 65                  70                  75                  80
```

```
Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
    130                 135                 140

Asp Glu Ile Asp Ile Thr Asn Ala Asp Ser Ile Thr Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Asn Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
        355

<210> SEQ ID NO 11
<211> LENGTH: 461
<212> TYPE: PRT
<213> ORGANISM: Curtobacterium oceanosedimentum

<400> SEQUENCE: 11

Ala Asp Arg Asn Thr Ser Ala Ala Glu Ala Ala Val Thr Ser Ile Ala
1               5                   10                  15

Pro Arg Ala Thr Ile Thr Gly Val Ala Ala Ile Ser Ala Ala Thr Ser
                20                  25                  30

Ser Arg Thr Thr Val Arg Thr Thr Leu Thr Leu Glu Asn Arg Ser Gly
            35                  40                  45

Glu Arg Glu Ser Ala Ala Asp Ala Trp Leu Tyr Leu Ala Gly Gly Gly
        50                  55                  60

Ala Arg Tyr Ala Leu Gly His Ala Pro Val Arg Ala Leu Ala Ala Gly
65                  70                  75                  80

Ala Arg Ala Thr Val Arg Thr Thr Leu Arg Val Pro Ser Arg Ala Pro
```

|    |    |    |    |    |    |    |    |    |    |    |    |    |    |    |
|---|---|---|---|---|---|---|---|---|---|---|---|---|---|---|
|    |    |    | 85 |    |    |    | 90 |    |    |    | 95 |    |    |    |
| Ala | Gly | Lys | Tyr | Ala | Val | Leu | Ala | Cys | Ala | Gly | Pro | Tyr | Ser | Lys | Gln |
|    |    |    | 100 |    |    |    | 105 |    |    |    | 110 |    |    |    |
| Ala | Cys | Arg | Thr | Ser | Gly | Thr | Thr | Val | Thr | Val | Gly | Thr | Ala | Ala | Arg |
|    |    |    | 115 |    |    |    | 120 |    |    |    | 125 |    |    |    |
| Ala | Arg | Pro | Glu | Thr | Gly | Val | Met | Leu | Asp | Val | Ala | Arg | Ala | Tyr | Tyr |
| 130 |    |    |    |    | 135 |    |    |    |    | 140 |    |    |    |    |    |
| Pro | Val | Ser | Leu | Ile | Glu | Gln | Tyr | Val | Asp | Leu | Leu | Ala | Glu | His | Gly |
| 145 |    |    |    |    | 150 |    |    |    |    | 155 |    |    |    |    | 160 |
| Gly | Gly | Phe | Leu | His | Leu | His | Leu | Thr | Asp | Asp | Gln | Asn | Val | Gly | Ile |
|    |    |    |    | 165 |    |    |    |    | 170 |    |    |    |    | 175 |    |
| Glu | Ser | Ala | Val | Leu | Gly | Gln | Thr | Pro | Ala | Asn | Ala | Val | Leu | Arg | Asn |
|    |    |    | 180 |    |    |    |    | 185 |    |    |    |    | 190 |    |    |
| Gly | Val | Tyr | Thr | Ser | Arg | Val | Thr | Gly | Arg | Pro | Phe | Leu | Ser | Ala | Ala |
|    |    | 195 |    |    |    |    | 200 |    |    |    |    | 205 |    |    |    |
| Gln | Ala | Arg | Ala | Ile | Ser | Ala | Tyr | Ala | Ala | Lys | Arg | Gly | Ile | Ala | Ile |
|    | 210 |    |    |    |    | 215 |    |    |    |    | 220 |    |    |    |    |
| Val | Pro | Glu | Val | Asp | Ser | Pro | Gly | His | Met | Ala | Ala | Ala | Phe | Ala | Leu |
| 225 |    |    |    |    | 230 |    |    |    |    | 235 |    |    |    |    | 240 |
| Leu | Glu | Ala | Arg | His | Gly | Ala | Thr | Trp | Val | Asp | Arg | Ile | Arg | Ser | Gly |
|    |    |    |    | 245 |    |    |    |    | 250 |    |    |    |    | 255 |    |
| Glu | Ser | Glu | Leu | Asp | Thr | Ser | Val | Pro | Glu | Ser | Ala | Thr | Leu | Ala | Ala |
|    |    |    | 260 |    |    |    |    | 265 |    |    |    |    | 270 |    |    |
| Glu | Leu | Leu | Arg | Glu | Val | Thr | Gln | Thr | Phe | Pro | Ser | Ser | Arg | Thr | Val |
|    |    | 275 |    |    |    |    | 280 |    |    |    |    | 285 |    |    |    |
| His | Ile | Gly | Gly | Asp | Glu | Trp | Gly | Ala | Asp | Val | Ser | Ala | Asp | Glu | Arg |
|    | 290 |    |    |    |    | 295 |    |    |    |    | 300 |    |    |    |    |
| Val | Gly | Trp | Met | Asn | Ala | Met | Ala | Ala | Ile | Gly | Asp | Arg | Glu | Val |
| 305 |    |    |    |    | 310 |    |    |    |    | 315 |    |    |    |    | 320 |
| Trp | Ala | Trp | Asn | Asp | Gly | Ile | Asp | Arg | Ala | Ser | Val | Gly | Arg | Leu | Asp |
|    |    |    |    | 325 |    |    |    |    | 330 |    |    |    |    | 335 |    |
| Pro | Arg | Ile | His | Val | Thr | Tyr | Trp | Ser | Phe | Asp | Gly | Asp | Thr | Glu | Asp |
|    |    |    | 340 |    |    |    |    | 345 |    |    |    |    | 350 |    |    |
| Ala | Ala | Glu | Arg | Arg | Glu | Arg | Ala | Arg | Arg | Ala | Ser | Ala | Thr | Asp |
|    |    | 355 |    |    |    |    | 360 |    |    |    |    | 365 |    |    |    |
| Leu | Gln | Arg | Ala | Gly | Ile | Asp | Leu | Leu | Asn | Tyr | Asn | Ser | Tyr | Tyr | Leu |
|    | 370 |    |    |    |    | 375 |    |    |    |    | 380 |    |    |    |    |
| Tyr | Glu | Val | Pro | Thr | Asp | Leu | Asp | Pro | Ala | Asp | Ser | Glu | Tyr | Thr | Val |
| 385 |    |    |    |    | 390 |    |    |    |    | 395 |    |    |    |    | 400 |
| Ala | Asp | Leu | Arg | Glu | His | Trp | Ser | Leu | Arg | Ala | Trp | Asp | Gly | Asp | Ser |
|    |    |    |    | 405 |    |    |    |    | 410 |    |    |    |    | 415 |    |
| Gly | Ala | Arg | Leu | Ala | Ala | Pro | Met | Ser | Gly | Ala | Ala | Val | Ala | Ile | Trp |
|    |    |    | 420 |    |    |    |    | 425 |    |    |    |    | 430 |    |    |
| Gly | Glu | Asp | Leu | Asp | Gly | Ala | Pro | Ser | Glu | Ala | Leu | Leu | Arg | Trp | Ser |
|    |    | 435 |    |    |    |    | 440 |    |    |    |    | 445 |    |    |    |
| Ala | Pro | His | Val | Thr | Ala | Met | Ile | Glu | Thr | Ala | Ala | Ser |    |    |    |
|    | 450 |    |    |    |    | 455 |    |    |    |    | 460 |    |    |    |    |

<210> SEQ ID NO 12
<211> LENGTH: 324
<212> TYPE: PRT
<213> ORGANISM: Terribacillus saccharophilus

<400> SEQUENCE: 12

```
Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
            35                  40                  45

Ala Ser Glu Phe Leu Gly Gln Asn Ser Glu Asn Pro Asn Ser Ala Tyr
50                  55                  60

Leu Thr Lys Lys Glu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
            115                 120                 125

Ala Leu Tyr Thr Ala Asn Gln Leu Leu Asp Glu Val Leu Asp Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
                180                 185                 190

Trp Asn Asp Ser Ile Thr Pro Glu Gly Ile Gln Asn Leu Asp Arg Ser
                195                 200                 205

Phe Ser Ile Leu Tyr Trp Lys Gln Ser Thr Leu Ser Asn Gly Ala Gln
210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
                260                 265                 270

Asn Lys Phe Phe Tyr Ile Ser Asp Tyr Tyr Lys Gln Val Asp Thr Pro
                275                 280                 285

Asn Val Lys Gly Ser Ser Leu Val Phe Trp Gly Glu His Ala Asn Asp
                290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 13
<211> LENGTH: 324
<212> TYPE: PRT
<213> ORGANISM: Terribacillus goriensis

<400> SEQUENCE: 13

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
            20                  25                  30

Gly Asp Tyr Leu Gln Leu His Phe Ser Asp Asn Glu Arg Tyr Ala Ile
            35                  40                  45
```

Ala Ser Glu Phe Leu Gly Gln Asn Gly Glu Asn Pro Asn Ser Thr Tyr
 50                  55                  60

Leu Thr Lys Lys Glu Leu Leu Ser Leu Ile Ala Tyr Ser Asn Asp Arg
 65                  70                  75                  80

Asp Ile Met Val Ile Pro Asp Ile Asp Leu Pro Ala His Ser Arg Gly
                 85                  90                  95

Trp Leu Asn Ile Met Lys Glu Lys Asp Ser Gly Leu Tyr Thr Asp Ile
                100                 105                 110

Val Thr Asp Tyr Ser Glu Asp Thr Leu Asp Tyr His Asn Asn Ala Val
                115                 120                 125

Ala Leu Tyr Thr Ala Asn Gln Leu Leu Asp Glu Val Leu Asp Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
                180                 185                 190

Trp Asn Asp Ser Ile Thr Pro Glu Gly Ile Gln Asn Leu Asp Arg Ser
                195                 200                 205

Phe Ser Ile Leu Tyr Trp Lys Gln Ser Thr Leu Ser Asn Gly Ala Gln
210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
                260                 265                 270

Asn Lys Phe Phe Tyr Ile Ser Asp Tyr Tyr Lys Gln Val Asp Thr Ser
                275                 280                 285

Asn Val Lys Gly Ser Ser Leu Val Phe Trp Gly Glu His Ala Asn Asp
                290                 295                 300

Leu Ser Gln Glu Gly Leu Leu Lys Gln Glu Lys Pro Leu Ile Gln Asn
305                 310                 315                 320

Phe Leu Gly Leu

<210> SEQ ID NO 14
<211> LENGTH: 324
<212> TYPE: PRT
<213> ORGANISM: Terribacillus saccharophilus

<400> SEQUENCE: 14

Lys Asp Gln Glu Lys Gly Ile Thr Ile Asp Ile Ser Arg Lys Tyr Tyr
 1                   5                  10                  15

Ser Ile Gly Thr Leu Lys Ala Ile Val Asp Glu Ile Asn Ala Asn Gly
                 20                  25                  30

Gly Asp Tyr Leu Gln Leu His Phe Ser Asp Asn Glu Ser Tyr Ala Ile
                 35                  40                  45

Ala Ser Glu Phe Leu Gly Gln Asn Ser Glu Asn Pro Asn Ser Thr Tyr
 50                  55                  60

Leu Thr Lys Lys Glu Leu Leu Ser Leu Ile Ala Tyr Ser Asn Asp Arg
 65                  70                  75                  80

Asn Ile Met Val Ile Pro Asp Ile Asp Leu Pro Ala His Ser Lys Gly
                 85                  90                  95

```
Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Ser Gly Ala Gln
210                 215                 220

Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
290                 295                 300

Leu Ser Gln Glu Gly Leu Leu Glu Gln Glu Lys Pro Leu Ile Gln Asn
305                 310                 315                 320

Phe Leu Ser Leu

<210> SEQ ID NO 15
<211> LENGTH: 445
<212> TYPE: PRT
<213> ORGANISM: Curtobacterium flaccumfaciens

<400> SEQUENCE: 15

Asp Thr Ala Val Ser Ala Val Thr Val Thr Lys Val Thr Ala Ser Thr
1               5                   10                  15

Thr Gly Thr Val Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
        35                  40                  45

Glu Lys Tyr Thr Leu Gly Arg Val Ala Val Lys Ala Leu Ala Ala Gly
    50                  55                  60

Ser Ser Thr Ser Val Thr Ala Val Arg Gly Thr Pro Ser Arg Ala Ala
65                  70                  75                  80

Ala Gly Lys Tyr Ser Val Leu Ala Cys Ala Gly Ala Tyr Ser Ala Lys
                85                  90                  95

Gln Cys Arg Thr Ser Thr Ala Thr Val Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140
```

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Ala Tyr Gly Ala Glu Arg Gly Val Ala Ile
        195                 200                 205

Val Pro Glu Ile Asp Thr Pro Gly His Met Ala Ala Phe Ala Leu
210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Ala Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Val Thr Ala Ala Gln Arg
        275                 280                 285

Val Thr Trp Met Asn Ala Met Ala Ala Leu Asp Asp Arg Glu Val
290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
                325                 330                 335

Ala Ala Glu Arg Arg Glu Arg Arg Ala Arg Arg Ala Ser Ala Val Asp
            340                 345                 350

Leu Gln Gln Ala Gly Ile Asp Gln Leu Asn Tyr Asn Ser Tyr Tyr Leu
        355                 360                 365

Tyr Glu Val Pro Thr Asp Leu Asp Pro Ala Asp Ser Asp Tyr Thr Val
370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
        435                 440                 445

<210> SEQ ID NO 16
<211> LENGTH: 445
<212> TYPE: PRT
<213> ORGANISM: Curtobacterium luteum

<400> SEQUENCE: 16

Asp Thr Ala Val Ser Ala Val Thr Val Thr Lys Val Thr Ala Ser Thr
1               5                   10                  15

Thr Gly Thr Ala Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
        35                  40                  45

Glu Lys Tyr Thr Leu Gly Arg Val Ala Val Lys Ala Leu Ser Ala Gly
    50                  55                  60

Ser Ser Thr Ser Val Thr Ala Val Arg Gly Thr Pro Ser Arg Ala Ala
65                  70                  75                  80

Ala Gly Lys Tyr Trp Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Glu Tyr Gly Ala Glu Arg Gly Val Thr Ile
        195                 200                 205

Val Pro Glu Ile Asp Thr Pro Gly His Met Ala Ala Ala Phe Ala Leu
    210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Val Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Asp Val Thr Ala Ala His Arg
        275                 280                 285

Val Ala Trp Met Asn Glu Met Ala Ala Thr Leu Gly Asn Arg Glu Val
    290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
                325                 330                 335

Ala Ala Glu Arg Arg Glu Arg Arg Ala Arg Ala Ser Ala Val Asp
        340                 345                 350

Leu Gln Gln Ala Gly Ile Asp Gln Leu Asn Tyr Asn Ser Tyr Tyr Leu
    355                 360                 365

Tyr Glu Val Pro Thr Asp Leu Asp Pro Ala Asp Ser Asp Tyr Thr Val
    370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
        435                 440                 445

<210> SEQ ID NO 17
<211> LENGTH: 458
<212> TYPE: PRT
<213> ORGANISM: Curtobacterium oceanosedimentum

<400> SEQUENCE: 17

Ile Gly Gly Ser Ala Gly Thr Ala Asp Ala Ser Gly Ala Pro Arg Leu

-continued

```
1               5                   10                  15
Val Val Thr Lys Val Thr Ala Ser Ser Thr Thr Thr Ser Thr Arg Thr
            20                  25                  30

Thr Val Arg Thr Thr Leu Thr Val Lys Asn Thr Ser Val Ala Arg Lys
            35                  40                  45

Pro Ala Ala Asp Ala Trp Leu Ser Leu Thr Ala Gly Ser Lys Arg Tyr
            50                  55                  60

Thr Leu Gly His Val Ser Val Gln Ser Leu Ala Ala Gly Ala Ser Ala
65                  70                  75                  80

Thr Ile His Ala Thr His Thr Ala Pro Pro Arg Ala Pro Ala Gly Lys
                85                  90                  95

Tyr Ala Val Leu Ala Cys Thr Gly Ala Phe Ser Leu Ser Lys Cys Gly
                100                 105                 110

Thr Ser Ala Thr Thr Val Thr Thr Ala Arg Ala Thr Arg Ala Arg Pro
                115                 120                 125

Asp Thr Gly Val Met Leu Asp Val Ala Arg Ala Tyr Tyr Pro Val Ala
130                 135                 140

Leu Ile Glu Gln Tyr Ile Ala Leu Leu Ala Asp His Gly Gly Arg Phe
145                 150                 155                 160

Leu His Leu His Leu Thr Asp Asp Gln Asn Val Gly Ile Glu Ser Glu
                165                 170                 175

Val Leu Gly Gln Thr Leu Ala Asn Ala Asp Leu Arg Asp Gly Val Tyr
                180                 185                 190

Thr Ser Arg Ile Thr Gly Arg Pro Phe Leu Ser Ala Ala Gln Ala Arg
                195                 200                 205

Glu Ile Ser Arg Tyr Ala Ala Gln Arg Gly Ile Ala Ile Pro Glu
210                 215                 220

Ile Asp Thr Pro Gly His Met Ala Ala Ala Phe Ala Leu Leu Glu Ala
225                 230                 235                 240

Gly His Gly Lys Gln Trp Val Asp Arg Ile Arg Ser Gly Glu Ser Glu
                245                 250                 255

Leu Asp Thr Ser Ala Pro Gly Ser Ser Ala Leu Ala Ala Arg Leu Leu
                260                 265                 270

Gln Glu Val Thr Arg Thr Phe Pro Ser Ser Arg Thr Val His Ile Gly
                275                 280                 285

Gly Asp Glu Trp Gly Asp Asp Val Thr Ala Asp Glu Arg Val Gln Trp
290                 295                 300

Leu Asn Thr Met Ala Ala Ala Val Gly Asn Arg Ala Val Trp Ala Trp
305                 310                 315                 320

Asn Asp Gly Ile Asp Arg Ala Ala Ile Gly Arg Leu Asp Pro Arg Ile
                325                 330                 335

His Val Thr Tyr Trp Ser Phe Asp Gly Asp Thr Glu Ala Thr Glu
                340                 345                 350

Arg Arg Glu Arg Glu Arg Arg Ala Gly Ala Asn Asp Leu Tyr Ala
                355                 360                 365

Ala Gly Ile Asp Leu Leu Asn Tyr Asn Ser Tyr Tyr Leu Tyr Glu Val
370                 375                 380

Pro Thr Asp Leu Asp Ala Ala Asp Ser Glu Tyr Thr Val Ala Asp Leu
385                 390                 395                 400

Arg Glu Asn Trp Ser Leu Arg Thr Trp Asp Gly Asp Ser Gly Ala Arg
                405                 410                 415

Leu Ala Gly Pro Thr Ser Gly Ala Ala Val Ala Ile Trp Gly Glu Asp
                420                 425                 430
```

```
Leu Glu Ala Pro Pro Ser Asp Ala Leu Leu Arg Trp Ser Ala Pro His
            435                 440                 445

Val Leu Ala Met Ile Glu Thr Ala Gly Ser
    450                 455
```

<210> SEQ ID NO 18
<211> LENGTH: 450
<212> TYPE: PRT
<213> ORGANISM: Curtobacterium sp. Leaf154

<400> SEQUENCE: 18

```
Ala Gly Ser Thr Thr Ser Thr Val Thr Val Thr Gln Val Thr Ala Thr
1               5                   10                  15

Thr Thr Ala Ser Ser Thr Gly Thr Ala Val Arg Thr Thr Leu Lys Ile
            20                  25                  30

Lys Asn Thr Ala Ala Val Arg Lys Pro Ala Ser Ser Ala Trp Leu Tyr
            35                  40                  45

Leu Ser Ala Gly Thr Lys Lys Tyr Thr Leu Gly Arg Val Ala Val Lys
        50                  55                  60

Ala Leu Ala Ala Gly Ser Ser Thr Ser Val Thr Ala Val Arg Gly Thr
65                  70                  75                  80

Pro Ser Arg Ala Thr Ala Gly Glu Tyr Ser Val Leu Ala Cys Ala Gly
                85                  90                  95

Ala Tyr Ser Ala Lys Gln Cys Arg Thr Ser Thr Ala Thr Val Thr Thr
            100                 105                 110

Lys Pro Thr Lys Arg Ala Arg Pro Glu Thr Gly Val Met Leu Asp Val
        115                 120                 125

Ala Arg Ala Tyr Tyr Pro Val Ala Leu Ile Lys Arg Tyr Ile Asp Leu
130                 135                 140

Leu Ala Asp Asp Gly Gly Arg Phe Leu His Leu His Leu Thr Asp Asp
145                 150                 155                 160

Gln Asn Val Gly Ile Glu Ser Thr Val Leu Gly Gln Thr Leu Ala Asn
                165                 170                 175

Ala Asp Leu Asp Glu Gly Val Tyr Thr Ser Arg Val Thr Arg Arg Pro
            180                 185                 190

Phe Leu Ser Ala Ala Gln Ala Arg Thr Ile Ser Asp Tyr Ala Ala Arg
        195                 200                 205

Arg Gly Val Ala Ile Val Pro Glu Ile Asp Thr Pro Gly His Met Thr
210                 215                 220

Ala Ala Phe Asp Leu Leu Glu Ala Gln His Gly Thr Lys Trp Val Asp
225                 230                 235                 240

Arg Ile Arg Ser Gly Glu Asn Glu Leu Asp Thr Ser Thr Pro Gly Ser
                245                 250                 255

Leu Ala Leu Ala Lys Lys Leu Tyr Ala Glu Val Gln Arg Thr Phe Pro
            260                 265                 270

Ala Ser Arg Thr Val His Ile Gly Gly Asp Glu Trp Gly Asp Asp Val
        275                 280                 285

Ser Ala Ala Glu Arg Val Ala Trp Met Asn Ala Met Ala Ala Ala Leu
290                 295                 300

Gly Asn Arg Glu Val Trp Ala Trp Asn Asp Gly Ile Asp Arg Val Ala
305                 310                 315                 320

Val Gly Arg Leu Asp Pro Arg Ile His Val Thr Tyr Trp Ser Phe Asp
                325                 330                 335

Gly Asp Thr Glu Asp Ala Ala Glu Arg Arg Glu Arg Arg Ala Arg Arg
```

```
              340                 345                 350
Ala Ser Ala Val Asp Leu Gln Gln Ala Gly Ile Asp Met Leu Asn Tyr
        355                 360                 365

Asn Ser Tyr Tyr Leu Tyr Glu Val Pro Thr Asp Leu Asp Pro Ala Asp
        370                 375                 380

Ser Glu Tyr Thr Val Ala Asp Leu Arg Glu Asn Trp Ser Leu Arg Thr
385                 390                 395                 400

Trp Asp Gly Asp Ser Gly Ser Leu Leu Ala Ala Pro Met Ser Gly Ala
                405                 410                 415

Ala Val Ala Ile Trp Gly Glu Asp Leu Glu Asp Pro Pro Ser Asp Ala
                420                 425                 430

Leu Leu Arg Trp Ser Ala Pro His Val Thr Ala Met Ile Glu Thr Ala
        435                 440                 445

Ala Ser
    450
```

<210> SEQ ID NO 19
<211> LENGTH: 324
<212> TYPE: PRT
<213> ORGANISM: Terribacillus saccharophilus

<400> SEQUENCE: 19

```
Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys
65                  70                  75                  80

Asp Ile Leu Val Ile Pro Asp Ile Asp Leu Pro Ala His Ser Lys Gly
                85                  90                  95

Trp Leu Glu Leu Ile Lys Lys Lys Asp Val Lys Leu Tyr Asn Asp Ile
            100                 105                 110

Val Thr Asp Tyr Ser Glu Glu Thr Leu Asp Tyr Tyr Asp Asn Arg Val
        115                 120                 125

Ala Leu Asp Thr Val Asn Gln Leu Leu Asp Glu Val Leu Asp Leu Phe
    130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
            180                 185                 190

Trp Asn Asp Ser Ile Thr Ser Glu Gly Ile Ala Asn Leu Asp Asp Ser
        195                 200                 205

Phe Ser Ile Leu Tyr Trp Gln Gln Ser Thr Leu Ser Ser Gly Glu Glu
    210                 215                 220

Ser Leu Asn Val Glu Asp Phe Glu Asn Trp Gly Phe Ser Val Tyr Asn
225                 230                 235                 240

Tyr Asn Ala Tyr Ser Leu Tyr Phe Leu Pro Ser Asn Gly Phe Thr Gln
                245                 250                 255
```

```
Glu Asp Ile Asn Glu Gln Met Asp Tyr Met Asn Trp Ala Tyr Ala His
                260                 265                 270

Asn Lys Phe Phe Tyr Ile Ser Asp Tyr Tyr His Ala Val Glu Thr Ser
            275                 280                 285

Asn Val Lys Gly Ser Ser Leu Thr Phe Trp Gly Glu His Ala Thr Asp
        290                 295                 300

Leu Ser Gln Lys Lys Leu Leu Lys Gln Glu Leu Pro Leu Ile Arg His
305                 310                 315                 320

Tyr Leu Asn Leu

<210> SEQ ID NO 20
<211> LENGTH: 324
<212> TYPE: PRT
<213> ORGANISM: Terribacillus saccharophilus

<400> SEQUENCE: 20

Lys Asp Gln Glu Lys Gly Ile Ser Ile Asp Ile Ser Arg Lys Tyr Tyr
1               5                   10                  15

Ser Ile Gly Thr Leu Lys Ala Ile Ile Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Asp Tyr Leu Gly Gln Ile Ser Asp Thr Pro Asn Asn Thr Tyr
50                  55                  60

Leu Thr Lys Asn Asp Leu Leu Ser Leu Ile Ala Tyr Ser Asn Asp Arg
65                  70                  75                  80

Asn Ile Leu Ile Ile Pro Asp Met Asp Leu Pro Ala His Ser Arg Gly
                85                  90                  95

Trp Leu Glu Leu Met Lys Val Lys Asp Arg Glu Leu Tyr Thr Asp Ile
            100                 105                 110

Val Thr Asp Tyr Ser Asn Glu Thr Leu Asp Tyr His Asn Asn Thr Asp
        115                 120                 125

Ala Leu Asn Thr Ala Asn Gln Leu Leu Asn Glu Ile Leu Glu Leu Phe
130                 135                 140

Tyr Gln Pro Lys Phe Ala Gly Lys Gln Arg Ile Val Leu Gly Gly Asp
145                 150                 155                 160

Glu Val Pro Gly Ser Glu Ile His Gln Leu Asp Phe Ile Arg Phe Ile
                165                 170                 175

Asn Gln Ile Ala Ser Thr Ala Lys Ala Ser Asn Tyr Ala Pro Gln Met
            180                 185                 190

Trp Asn Asp Ser Ile Thr Ala Glu Gly Ile Gln Asn Leu Asp Lys Ser
        195                 200                 205

Phe Ser Ile Leu Tyr Trp Lys Gln Ser Thr Leu Ser Asn Gly Ala Gln
210                 215                 220

Ser Leu Glu Val Gln Asp Phe Glu Asp Trp Asp Phe Pro Val Tyr Asn
225                 230                 235                 240

Tyr Asn Ala Tyr Ser Leu Tyr Phe Leu Pro Ser Ile Arg Phe Thr Asp
                245                 250                 255

Glu Asp Ile Thr Glu Gln Met Asn Tyr Met Lys Trp Ala Tyr Ala Tyr
            260                 265                 270

Asn Lys Phe Phe Tyr Ile Ser Asp Tyr Tyr Lys Ser Val Asp Ala Ser
        275                 280                 285

Asn Val Lys Gly Ser Ser Leu Thr Phe Trp Gly Glu His Ala Thr Asp
290                 295                 300
```

```
Leu Ser Gln Glu Glu Leu Leu Glu Gln Glu Leu Pro Leu Ile Lys Lys
305                 310                 315                 320

Phe Leu Ser Leu
```

CLEANING COMPOSITIONS COMPRISING ENZYMES

CROSS-REFERENCE TO RELATED APPLICATIONS

This application is a 35 U.S.C. 371 national application of PCT/EP2017/063489 filed June 2, 2017, which claims priority or the benefit under 35 U.S.C. 119 of Denmark application PA 2016 00328 filed Jun. 3, 2016, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to cleaning (detergent) compositions comprising an enzyme having deoxyribonuclease (DNase) activity and an enzyme having hexosaminidase activity, a method for laundering a textile and the use of an enzyme having DNase activity together with an enzyme having hexosaminidase activity. The invention further relates to use of cleaning compositions comprising an enzyme having deoxyribonuclease (DNase) activity and an enzyme having hexosaminidase activity in cleaning processes.

BACKGROUND OF INVENTION

Some bacteria are capable of adhering to textiles (clothing) and forming a biofilm on the textile. Biofilm may be present on laundry items, such as fabrics, hard surfaces, such as dish wash utensils, dish washers and washing machines where they may cause malodor, which is difficult to remove even after wash. Biofilm may also make laundry items sticky and soil adheres to the sticky areas. Further, when very dirty laundry items are washed together with less dirty laundry items the dirt present in the wash liquor tend to stick to the biofilm.

Enzymes comprising hexosaminidase activity include chitinase and the use of such enzymes is described in WO9850512 (Proctor and Gamble). Enzymes having hexosaminidase activity include Dispersins such as Dispersin B (DspB), which as described is β-N-acetylglucosamininidases belonging to the Glycoside Hydrolase 20 family. WO04061117 A2 (Kane Biotech INC) describe compositions comprising DspB for reducing and preventing biofilm caused by poly-N-acetylglucosamine-producing bacteria and describes the use of the compositions comprising DspB for reduction/removing biofilm on medical devices and for wound care.

WO 2015/155350 (Novozymes A/S) discloses the use of a polypeptide having DNase activity for preventing, reducing or removing a biofilm component e.g. DNA from an item, wherein the polypeptide is obtained from a fungal source, such as *A. oryzae* and the item is a textile.

SUMMARY OF THE INVENTION

The present invention relates to a composition comprising an enzyme having DNase activity, an enzyme having hexosaminidase activity and an adjunct ingredient, wherein the hexosaminidase is selected from the group consisting of the DspB clade, the *Curtobacterium* clade and the *Terribacillus* clade. The invention further relates to the use of a such composition for deep cleaning of an item, wherein the item is a hard surface or a textile.

The invention further relates to a method for laundering an item comprising the steps of:
a. Exposing an item to a wash liquor comprising (i) an enzyme having DNase activity and an enzyme having hexosaminidase activity or (ii) a composition according to any of claims 1-18;
b. Completing at least one wash cycle; and
c. Optionally rinsing the item,
wherein the item is a textile.

The invention further relates to the use of a combination of an enzyme having DNase activity and an enzyme having hexosaminidase activity for deep cleaning an item, wherein the item is a textile or a hard surface.

Definitions

DNase (deoxyribonuclease): The term "DNase" means a polypeptide or an enzyme with DNase activity that catalyzes the hydrolytic cleavage of phosphodiester linkages in the DNA backbone, thus degrading DNA. For purposes of the present invention, DNase activity is determined according to the procedure described in the Assay II or Assay IIa. In one aspect, the DNase according to the present invention have at least 20%, e.g., at least 40%, at least 50%, at least 60%, at least 70%, at least 80%, at least 90%, at least 95%, or at least 100% of the DNase activity of the mature polypeptide of SEQ ID NO: 2. In one aspect the DNase of the present invention has at least 60%, e.g., at least 65%, at least 70%, at least 75%, at least 80%, at least 85%, at least 90%, at least 95%, or at least 100% sequence identity to the amino acid sequence having SEQ ID NO: 2.

Dispersin: The term "dispersin" and the abbreviation "Dsp" means a polypeptide having hexosaminidase activity, EC 3.2.1.—that catalyzes the hydrolysis of β-1,6-glycosidic linkages of N-acetyl-glucosamine polymers (poly-N-acetyl-glucosamine) found e.g. in biofilm. Hexosaminidase: The term "hexosaminidases" means a polypeptide having hexosaminidase activity (hexosaminidases), and includes EC 3.2.1. e.g. that catalyzes the hydrolysis of N-acetyl-D-hexosamine or N-acetyl-glucosamine polymers found e.g. in biofilm. The term includes dispersins and includes polypeptides having N-acetylglucosaminidase activity and β-N-acetylglucosamininidase activity. The term "polypeptide having hexosaminidase activity" may be used interchangeably with the term hexosaminidases and similar the term "polypeptide having β-N-acetylglucosaminidase activity" may be used interchangeably with the term β-N-acetylglucosamininidases. For purposes of the present invention, hexosaminidase activity is determined according to the procedure described in Assay I. In one aspect, the polypeptides of the present invention have at least 20%, e.g., at least 40%, at least 50%, at least 60%, at least 70%, at least 80%, at least 90%, at least 95%, or at least 100% of the hexosaminidase activity of the mature polypeptide of SEQ ID NO: 14.

Biofilm: A biofilm may be produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community. On laundry and hard surfaces biofilm producing bacteria can be found among the following species; *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. On hard surfaces biofilm producing bacteria may include but are not limited to the following species: *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus* and *Stenotrophomonas* sp. A wide range of bacterial and fungal microorganisms have been found to produce PNAG or PNAG-like surface polysaccharides, including but not limited to *Bacillus subtillis, Escherichia coli, Staphylococcus aureus, Staphylococcus epidermidis, Pseudomonas fluorescens, Yersinia pestis, Aggregatibacter actinomycetemcomitans, Streptococcus pyogenes, Streptococcus dysgalactiae* (group C strep), *Enterococcus faecalis, Listeria monocytogenes, Clostridium difficile, Mycobacterium tuberculosis, Mycobacterium smegmatis; Neisseria meningitides, Neisseria gonorrhea*, nontypable *Haemophilus influenzae, Haemophilus ducreyi, Helicobacter pylori, Campylobacter jejuni; Citrobacter rodentium, Salmonella enterica serovars typhi, Salmonella typhimurium, Candida albicans, Aspergillus flavus, Fusarium solani*, and *Cryptococcus neoformans*.

Extracellular DNA (eDNA) is a common matrix component in microbial biofilms and has been identified in, but not limited to, *Acinetobacter baumannii, Actinobacillus actinomycetemcomitans, Bdellovibrio bacterivorous, Bordetella pertussis, Bordetella bronchiseptica, Campylobacter jejuni, Comamonas denitrificans, Escherichia coli, Haemophilus influenza, Klebsiella pneumoniae, Neisseria meningitides, Pseudomonas aeruginosa, Shewanella oneidensis, Vibrio cholera*, Gram-positive bacteria, *Bacillus licheniformis, Bacillus subtilis, Enterococcus faecalis, Listeria monocytogenes, Micrococcus luteus, Staphylococcus aureus, Staphylococcus epidermidis, Staphylococcus haemolyticus, Streptococcus anginosus, Streptococcus constellatus, Streptococcus salivarius, Staphylococcus lugdunesis, Streptococcus intermedius, Streptococcus intermedius, Streptococcus mutans, Streptococcus pneumoniae, Streptococcus pyogenes, Aspergillus fumigatus* and *Candida albicans*.

Most biofilms comprises biofilm or EPS from bacteria of many different species and are thus "poly-cultural".

Clade a group of polypeptides clustered together based on homologous features traced to a common ancestor. Polypeptide clades can be visualized as phylogenetic trees and a clade is a group of polypeptides that consists of a common ancestor and all its lineal descendants e.g. the *Terribacillus* clade or clade of *Terribacillus* is a group of enzymes all related to the same ancestor and share common properties.

Coding sequence: The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Cleaning adjunct ingredient: The cleaning adjunct ingredient is an ingredient which is different from the enzymes comprised in the cleaning composition of this invention. The term includes the term "cleaning component" and is defined herein to mean the types of components which can be used in cleaning compositions. Examples of cleaning components are alkalis, surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants and solubilizers.

Cleaning composition: The term "cleaning composition" refers to compositions that find use in the removal of undesired compounds from textiles to be cleaned. The term includes detergent compositions. The cleaning composition may be used to e.g. clean textiles for both household cleaning and industrial cleaning. The terms encompass any materials/compounds selected for the cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pretreatment). In addition to containing the enzymes of the invention, the cleaning composition may contain one or more additional enzymes (such as proteases, amylases, lipases, cutinases, cellulases, endoglucanases, xyloglucanases, pectinases, pectin lyases, xanthanases, peroxidaes, haloperoxygenases, catalases and mannanases, or any mixture thereof), and/or cleaning components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Deep cleaning: By the term "deep cleaning" is meant reduction or removal of components of biofilm, such as EPS or parts hereof, polysaccharides, PNAG (poly-N-acetylglucosamine), proteins, DNA, soil or other components present in the biofilm.

Enzyme Detergency Benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or antibackstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Fungal: In the context of the present invention the term "fungal" in relation to polypeptide (such as an enzyme, e.g. a DNase) refers to a polypeptide encoded by and thus directly derivable from the genome of a fungus, where such fungus has not been genetically modified to encode said polypeptide, e.g. by introducing the encoding sequence in the genome by recombinant DNA technology. In the context of the present invention, the term "fungal DNase" or "polypeptide having DNase activity obtained from a fungal source" or "polypeptide is of fungal origin" thus refers to a DNase encoded by and thus directly derivable from the genome of a fungal species, where the fungal species has not been subjected to a genetic modification introducing recombinant DNA encoding said DNase. Thus, the nucleotide sequence encoding the fungal polypeptide having DNase activity is a sequence naturally in the genetic background of a fungal species. The fungal polypeptide having DNase activity encoding by such sequence may also be referred to a wildtype DNase. In one aspect of the invention the enzyme having DNase activity is substantially homologous to a fungal DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of SEQ ID NO 2.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the enzymes of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Malodor: By the term "malodor" is meant an odor which is not desired on clean items. The cleaned item should smell fresh and clean without malodors adhered to the item. One example of malodor is compounds with an unpleasant smell, which may be produced by microorganisms. Another example is unpleasant smells can be sweat or body odor adhered to an item which has been in contact with human or animal. Another example of malodor can be the odor from spices, which sticks to items such as curry or other exotic spices which smell strongly.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used, it is intended to include the broader term textiles as well. In the context of the present invention, the term "textile" also covers fabrics.

Variant: The term "variant" means a polypeptide/enzyme having the same activity as the parent enzyme comprising an alteration, i.e., a substitution, insertion, and/or deletion, at one or more positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant may be a variant of an identified DNase that has the enzymatic activity of the parent, i.e. the capacity of catalyzing the hydrolytic cleavage of phosphodiester linkages in the DNA backbone (deoxyribonuclease activity). In one embodiment, the deoxyribonuclease activity of the variant is increased with reference to the parent DNase, e.g. the polypeptide of SEQ ID NO: 2.

In the context of the present invention, a variant may also be a variant of an identified hexosaminidase that has the enzymatic activity of the parent, i.e. the capacity of catalyzing the hydrolysis of β-1,6-glycosidic linkages of N-acetyl-glucosamine polymers (hexosaminidase activity). In one embodiment, the hexosaminidase activity of the variant is increased with reference to the parent hexosaminidase, e.g. the polypeptide of SEQ ID NO: 14.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is intended to mean the solution or mixture of water and at least a surfactant, optionally including other detergent components e.g. enzymes other than the enzyme having DNase activity, and which is used for laundering textiles.

Wash performance: One way of measuring the wash performance is the Delta enzyme performance value (ΔRem enzyme value): The term "Delta enzyme remission value" is defined herein as the result of a reflectance or remission measurement at 460 nm. The remission value of a swatch is measured and compared to a swatch of similar colour as background, preferably a swatch from a repetition wash, with a swatch representing each type being measured before wash. The Delta enzyme remission is the remission value of the swatch washed in detergent with an enzyme present minus the remission value of a similar swatch washed in a detergent without enzyme present.

Another way of measuring the wash performance is by use of the Color difference (L value): A Lab color space is a color-opponent space with dimension L for lightness. The L value, L*, represents the darkest black at L*=0, and the brightest white at L*=100. In the context of the present invention L value is also referred to as color difference.

Whiteness: The term "whiteness" is defined herein as e.g. greying or yellowing e.g. textiles. Greying and yellowing can be due to soil redeposition, body soils, colouring from e.g. iron and copper ions or dye transfer.

DETAILED DESCRIPTION OF THE INVENTION

It was surprisingly found that washing textiles with an enzyme having DNase activity (DNase) in combination with an enzyme having hexosaminidase activity (Hexosaminidase) gives a surprisingly good result with regard to deep cleaning e.g., reduction/removing of biofilm components, maintaining whiteness and reducing redeposition of soil and malodor. A wide range of bacterial and fungal microorganisms have been found to produce PNAG or PNAG-like surface polysaccharides and most biofilms will comprise some amount of PNAG or PNAG-like surface polysaccharides since many different ubiquitous bacteria possess the ability to produce PNAG. DNA is also present in many biofilms. Therefore, DNA and PNAG is usually present in a biofilm including biofilms associated with cleaning such as laundry, washing machines, hard surfaces e.g. utensils etc. The present invention has therefore wide applications. One aspect of the invention relates to the use of a composition e.g. cleaning composition comprising a combination of an enzyme having DNase activity (DNase) and an enzyme having hexosaminidase activity (Hexosaminidase) for deep cleaning of an item e.g. reducing/removing biofilm components, wherein the biofilm components comprises PNAG and DNA. The biofilm components may be associated with textiles, such as clothing, washing machines, hard surfaces e.g. in ADW.

In one aspect, the biofilm or EPS producing strain is *Staphylococcus epidermidis*. In one aspect the biofilm or EPS producing strain is *Pseudomonas alcaliphila* or *Pseudomonas fluorescens*. In one aspect, the biofilm or EPS producing strain is *Staphylococcus aureus*. As described, adding a combination of enzymes having hexosaminidase activity e.g. Dispersins together with a DNase e.g. from *A. Oryzae*, such as a DNase with SEQ ID NO 2 or having at least 60% sequence identity hereto, is advantageous as the complex construction of biofilms gives rise to hidden pockets of PNAG and DNA inside the biofilm, pockets that are not available when only one enzyme is added. Applying the composition comprising the enzyme combination of the present invention provides better deep cleaning effect than by adding the single specificities. Surprisingly, it was found that adding a composition comprising the enzyme having hexosaminidase activity and the enzyme having DNase activity at the same time provides a synergistic effect e.g. as each enzymes' specific action releases more biofilm component than if the enzymes were added separately, see e.g. example 2 and 3. Thus, one aspect of the invention relates to the use of a composition comprising a hexosaminidase and a DNase for deep cleaning of an item, wherein a synergistic deep cleaning effect is obtained.

Further, this synergistic effect was shown in a detergent on e.g. on textiles such as laundry items. In one aspect of the invention the combination of the enzyme having hexosaminidase activity e.g. the dispersins and the enzyme having DNase activity e.g. the *A. oryzae* DNase provides synergistic deep cleaning effect in a detergent and is thus particularly useful in cleaning applications such as laundry and hard surface cleaning e.g. ADW (automatic dish washing).

One aspect relates to a method for laundering an item comprising the steps of:
a) Exposing an item to a wash liquor comprising an enzyme having DNase activity and enzyme having hexosaminidase activity or a composition according to the invention;
b) Completing at least one wash cycle; and
c) Optionally rinsing the item.

One aspect of the invention relates to a method of laundering a textile, comprising the steps of:
a) Contacting the textile with a wash liquor comprising an enzyme having DNase activity, an enzyme having hexosaminidase activity and a surfactant; and
b) optionally rinsing the textile,
wherein the enzyme having DNase activity and the hexosaminidase activity have deep cleaning properties.

In a wash liquor the concentration of each of the DNase and hexosaminidase is preferably at least 0.00001 mg/L or at least 0.0001 or at least 0.001 mg/L of enzyme or at least 0.01, 0.02, 0.05, 0.1, 0.2, 0.5, 1, 2, 5, 10 or at least 15 µg active enzyme per liter of wash liquor. Optionally the concentration of enzyme in the wash liquor is in the range of about 0.00002 mg/L to about 2 mg/L, about 0.0002 mg/L to about 2 mg/L, about 0.002 mg/L to about 2 mg/L, such as about 0.02 mg/L to about 2 mg/L, such as about 0.2 mg/L to about 2 mg/L or in the range of about 0.00001 mg/L to about 1 mg/L, about 0.0001 mg/L to about 1 mg/L, about 0.0001 mg/L to about 10 mg/L or in the range of in the range of about 0.001 mg/L to about 10 mg/L, or in the range of about 0.01 mg/L to about 10 mg/L, or in in the range of about 0.1 mg/L to about 10 mg/L per liter of wash liquor.

In one aspect, the biofilm comprises at least one bacterium having the polysaccharide poly-N-acetylglucosamine (PNAG) on the outer surface. In one aspect, such bacteria are *Pseudomonas fluorescens*. In one aspect such bacteria is *staphylococcus aureus* and the biofilm or EPS comprises PNAG. Enzymes having hexosaminidase activity, such as Dispersins, hydrolyze β-1,6-glycosidic linkages of N-acetyl-glucosamine polymers, and compositions comprising Dispersin B (DspB) is described in WO200406117. However, to be useful in cleaning processes enzymes need to perform their action under the conditions of cleaning processes such as laundry, which includes stability in the presence of cleaning components such as surfactants, builders and bleach components. There is no indication in the art of the use of hexosaminidases, such as dispersins, in combination with DNases in cleaning processes such as laundry or in detergent compositions comprising adjuncts e.g. surfactants, builders and/or bleaches.

Thus, some aspects of the invention relate the use of an enzyme having DNase activity and an enzyme having hexosaminidase activity in a cleaning process. Some aspects of the invention relates to cleaning compositions comprising a) an enzyme having DNase activity and an enzyme having hexosaminidase activity and b) at least one surfactant, preferably at least one surfactant selected from the group consisting of anionic, nonionic and/or cationic surfactants.

Some aspects of the present invention relate to laundry or cleaning compositions comprising a DNase and a hexosaminidase enzyme, preferably at a level of from about 0.000001 wt % to about 1 wt %, from about 0.0001 wt % to about 1 wt %, from about 0.0002 wt % to about 1 wt %, from about 0.0005 wt % to about 1 wt %, from about 0.001 wt % to about 1 wt %, from about 0.002 wt % to about 1 wt %, from about 0.005 wt % to about 1 wt %, preferably from about 0.01 wt % to about 0.5 wt %, preferably from 0.0002 wt % to about 1 wt % by weight (wt %) of the composition. The amounts are wt % per unit active enzyme e.g. from about 0.00001 wt % to about 1 wt % of DNase by weight of the composition and from about 0.00001 wt % to about 1 wt % of hexosaminidase by weight of the composition.

The concentration of the active enzyme having hexosaminidase activity is preferably at least 0.00001%, preferably at least 0.00002%, preferably at least 0.0001 wt %, preferably at least 0.0002 wt %, preferably at least 0.001 wt %, preferably at least 0.002 wt %, preferably at least 0.005 wt %, preferably at least 0.01 wt %, preferably at least 0.02 wt %, preferably at least 0.05 wt % preferably at least 0.1 wt % of the total detergent concentration.

The concentration of the active enzyme having DNase activity is preferably at least 0.00001%, preferably at least 0.00002%, preferably at least 0.0001 wt %, preferably at least 0.0002 wt %, preferably at least 0.001 wt %, preferably at least 0.002 wt %, preferably at least 0.005 wt %, preferably at least 0.01 wt %, preferably at least 0.02 wt %, preferably at least 0.05 wt % preferably at least 0.1 wt % of the total detergent concentration.

The amount enzyme may also be in ppm (mg/L) active enzyme protein. Thus, in one aspect the amount of DNase in the composition is at least 0.00001 ppm, 0.00002 ppm, 0.00005 ppm, 0.0001 ppm, 0.0002 ppm, 0.0005 ppm, 0.001 ppm, 0.002 ppm, 0.005 ppm, 0.01 ppm, 0.02 ppm, 0.05 ppm, 0.1 ppm, 0.2 ppm, 0.5 ppm, 1 ppm, 2 ppm, 5 ppm, 10 ppm or at least 20 ppm DNase enzyme. In one aspect, the amount of DNase in the composition is in the range from about 0.00001 ppm to about 10 ppm, or in the range from about 0.0001 ppm to about 2 ppm or in the range from about 0.001 ppm to about 2 ppm DNase enzyme.

In one aspect the amount of hexosaminidase in the composition is at least 0.00001 ppm, 0.00002 ppm, 0.00005 ppm, 0.0001 ppm, 0.0002 ppm, 0.0005 ppm, 0.001 ppm, 0.002 ppm, 0.005 ppm, 0.01 ppm, 0.02 ppm, 0.05 ppm, 0.1 ppm, 0.2 ppm, 0.5 ppm, 1 ppm, 2 ppm, 5 ppm, 10 ppm or at least 20 ppm hexosaminidase enzyme. In one aspect, the amount of hexosaminidase in the composition is in the range from about 0.00001 ppm to about 10 ppm, or in the range from about 0.0001 ppm to about 2 ppm or in the range from about 0.001 ppm to about 2 ppm hexosaminidase enzyme.

In one aspect, the ratio of DNase to hexosaminidase is 1:2, such as 1:3, such as 1:4, such as 1:5, such as 1:6, such as 1:7, such as 1:8, such as 1:9, such as 1:10.

In one aspect, the ratio of hexosaminidase to DNase is 1:2, such as 1:3, such as 1:4, such as 1:5, such as 1:6, such as 1:7, such as 1:8, such as 1:9, such as 1:10.

Preferably the amount of hexosaminidase enzyme is higher than the amount of DNase in cleaning composition of the invention.

In the compositions, e.g. cleaning composition, the enzyme levels are expressed by pure enzyme by weight of the total composition unless otherwise specified and the adjunct ingredients are expressed by weight of the total composition.

One aspect of the invention relates to a cleaning composition comprising:

a) at least 0.0001 wt % e.g. 0.001 wt % of an enzyme having DNase activity and at least 0.0001 wt % e.g. 0.001 wt % of an enzyme having hexosaminidase activity, and b) from about 0 wt % to about 60 wt % surfactant, preferably from about 5 wt % to about 60 wt %, preferably from about 10 wt % to about 60 wt %, preferably from about 15 wt % to about 60 wt %, wherein the surfactant is selected from anionic, nonionic and/or cationic surfactants.

The surfactant may be selected among nonionic, cationic, anionic and/or amphoteric surfactants as described above, preferably anionic or nonionic surfactants but also cationic or amphoteric surfactants may be used. In general, bleach-stable surfactants are preferred. Preferred anionic surfactants are sulphate surfactants and alkyl ether sulphates, especially C9-C15 alcohol ethersulfates, C12-C15 primary alcohol ethoxylate, C8-C16 ester sulphates and C10-C14 ester sulphates, such as mono dodecyl ester sulphates. Non-limiting examples of anionic surfactants include sulfates and sulfonates, in particular linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salts of fatty acids (soap), and combinations thereof.

The anionic surfactants are preferably added to the detergent in the form of salts. Suitable cations in these salts are alkali metal ions, such as sodium, potassium and lithium and ammonium salts, for example (2-hydroxyethyl) ammonium, bis (2-hydroxyethyl) ammonium and tris (2-hydroxyethyl) ammonium salts.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN® and TWEEN®, and combinations thereof. Commercially available nonionic surfactants include Plurafac™, Lutensol™ and Pluronic™ range from BASF, Dehypon™ series from Cognis and Genapol™ series from Clariant. In one aspect, the surfactant is non-natural i.e. not found in nature.

The cleaning composition of the invention may optionally comprise a builder and in one aspect of the invention the cleaning composition is a laundry (powder or liquid) or ADW composition comprising:

a) at least 0.0001 wt % e.g. 0.001 wt % of an enzyme having DNase activity and at least 0.0001 wt % e.g. 0.001 wt % of an enzyme having hexosaminidase activity, and optionally b) from about 0 wt % to about 60 wt % surfactant, preferably from about 5 wt % to about 60 wt %, preferably from about 10 wt % to about 60 wt %, preferably from about 15 wt % to about 60 wt %, wherein the surfactant is selected from anionic, nonionic and/or cationic surfactants, and optionally c) from about 0 wt % to about 50 wt % of at least one builder, preferably from about 5 wt % to about 50 wt %, preferably from about 10 wt % to about 50 wt %, preferably from about 15 wt % to about 50 wt %, wherein the builder preferably is selected from carbonates, zeolites, phosphate builder, calcium sequestering builders or complexing agents.

The builder is preferably selected among phosphates, sodium citrate builders, sodium carbonate, sodium silicate, and sodium aluminosilicate (zeolite). Suitable builders are alkali metal or ammonium phosphates, polyphosphates, phosphonates, polyphosphonates, carbonates, bicarbonates, borates, citrates, and polycarboxylates. Citrate builders, e.g., citric acid and soluble salts thereof (particularly sodium salt), are polycarboxylate builders. Citrates can be used in combination with zeolite, silicates like the BRITESIL types, and/or layered silicate builders. The builder is preferably added in an amount of about 0-65% by weight, such as about 5% to about 50% by weight. In the composition of the invention, the level of builder is typically about 40-65% by weight, particularly about 50-65% by weight, particularly from 20% to 50% by weight. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), and (carboxymethyl)inulin (CMI), and combinations thereof. Further non-limiting examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl) aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof.

Phosphonates suitable for use herein include 1-hydroxyethane-1,1-diphosphonic acid (HEDP), ethylenediaminetetrakis (methylenephosphonic acid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), and hexamethylenediaminetetrakis (methylenephosphonic acid) (HDTMP)

The composition of the invention may also contain 0-50% by weight, such as about 5% to about 30%, of a detergent co-builder. The composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid. Further exemplary builders and/or co-builders are described in, e.g., WO 09/102854, U.S. Pat. No. 5,977,053. In one preferred embodiment, the builder is a non-phosphorus based builder such as citric acid and/or methylglycine-N, N-diacetic acid (MGDA) and/or glutamic-N, N-diacetic acid (GLDA) and/or salts thereof.

One aspect of the invention relates a composition comprising at least one enzyme having DNase activity and at least one enzyme having hexosaminidase activity and a non-phosphate builder selected from citric acid, methyl glycine-N, N-diacetic acid (MGDA) and/or glutamic-N, N-diacetic acid (GLDA) and mixtures thereof.

In one aspect, the composition is cleaning composition, such as a laundry composition or an automatic dish wash composition (ADW) comprising:

a) at least 0.0001 wt % e.g. 0.001 wt % of an enzyme having DNase activity and at least 0.0001 wt %, e.g. 0.001 wt % of an enzyme having hexosaminidase activity, and b) from about 0 wt % to about 50 wt % of at least one builder, preferably from about 5 wt % to about 50 wt %, preferably from about 10 wt % to about 50 wt %, preferably from about 15 wt % to about 50 wt %, wherein the builder preferably is selected from carbonates, zeolites, phosphate builder, calcium sequestering builders or complexing agents, preferably citric acid, methylglycine-N, N-diacetic acid (MGDA) and/or glutamic acid-N, N-diacetic acid (GLDA) and mixtures thereof, and optionally c) at least one bleach component.

The composition may contain 0-30% by weight, such as about 1% to about 20%, such as about 1% to about 10%, such as about 1% to about 5%, such as about 10% to about 30%, such as about 5% to about 10% or such as about 10% to about 20% by weight (wt %) of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl) oxy] benzene-1-sulfonate (ISONOBS), sodium 4-(dodecanoyloxy) benzene-1-sulfonate (LOBS), sodium 4-(decanoyloxy) benzene-1-sulfonate, 4-(decanoyloxy) benzoic acid (DOBA), sodium 4-(nonanoyloxy) benzene-1-sulfonate (NOBS), and/or those disclosed in WO98/17767. A family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytic stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, where a source of a peracid is included, an organic bleach catalyst or bleach booster may be used having one of the following formulae:

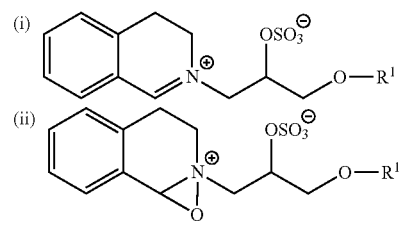

or mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g., in WO2007/087258, WO2007/087244, WO2007/087259, EP1867708 (Vitamin K) and WO2007/087242. Suitable photobleaches may for example be sulfonated zinc or aluminium phthalocyanines.

The present invention relates to cleaning compositions e.g. detergent compositions comprising at least one enzyme having DNase activity and at least one enzyme having hexosaminidase activity, compositions e.g. detergent compositions, and the use of cleaning e.g. detergent compositions of the invention for deep cleaning of an item such as a textile.

Accordingly, some aspects of the invention relate to cleaning compositions comprising:

a) at least 0.0001 wt % e.g. 0.001 wt % of an enzyme having DNase activity and at least 0.0001 wt % e.g. 0.001 wt % of an enzyme having hexosaminidase activity, and optionally b) from about 0 wt % to about 50 wt % of at least one builder, preferably from about 5 wt % to about 50 wt %, preferably from about 10 wt % to about 50 wt %, preferably from about 15 wt % to about 50 wt %, wherein the builder preferably is selected from carbonates, zeolites, phosphate builder, calcium sequestering builders or complexing agents, preferably citric acid, methylglycine-N, N-diacetic acid (MGDA) and/or glutamic acid-N, N-diacetic acid (GLDA) and mixtures thereof, and optionally c) from about 0 wt % to about 60 wt % surfactant, preferably from about 5 wt % to about 60 wt %, preferably from about 10 wt % to about 60 wt %, preferably from about 15 wt % to about 60 wt %, wherein the surfactant is selected from anionic, nonionic and/or cationic surfactants, preferably selected from anionic surfactants such as LAS, AOS, AEOS and/or nonionic surfactants such as AE or AEO, and optionally d) from about 0 or 30 wt %, preferably from about 5% to about 30%, preferably from about 10% to about 30% by weight (wt %) of at least one bleach component, preferably selected from percarbonates, persulphates and peracids, preferably percarbonate or a manganese catalyst, preferably 1,4,7-trimethyl-1,4,7-triazacyclononane or manganese (III) acetate tetrahydrate (MnTACN).

The enzymes having hexosaminidase activity to be used in the cleaning composition of the invention, which are useful for deep cleaning of items such as hard surfaces, textiles and/or fabric, are selected from hexosaminidases from the DspB clade, the *Curtobacterium* clade and the *Terribacillus* clade. In one aspect, the hexosaminidase is selected from the DspB clade. In one aspect the hexosaminidase is selected from any of the polypeptides having SEQ ID NOS 3, 4, 5, 6, 7, 8, 9, and 10 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. The enzymes having hexosaminidase activity have β-N-acetylglucosamininidase activity, β-1,6-N-acetylglucosaminidase activity and in some aspects, the hexosaminidase activity is β-1,6-N-acetylglucosaminidase activity and the enzymes of the invention are β-1,6-N-acetylglucosaminidases. One aspect of the invention relates to cleaning compositions comprising hexosaminidases from the DspB clade, except for SEQ ID NO 10. Thus, in one aspect the hexosaminidase is not the hexosaminidase with SEQ ID NO 10.

In one aspect, the enzymes having hexosaminidase activity to be used in the cleaning composition of the invention, which are useful for deep cleaning of items such as hard surfaces, textiles and/or fabric, are selected from hexosaminidases from the *Curtobacterium* clade. In one aspect, the hexosaminidase is a polypeptide with SEQ ID NO 11 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

In one aspect, the hexosaminidase is a polypeptide with SEQ ID NO 15 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

In one aspect, the hexosaminidase is a polypeptide with SEQ ID NO 16 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

In one aspect, the hexosaminidase is a polypeptide with SEQ ID NO 17 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

In one aspect, the hexosaminidase is a polypeptide with SEQ ID NO 18 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

In another aspect, the enzymes having hexosaminidase activity to be used in the cleaning composition of the invention, which are useful for deep cleaning of items such as hard surfaces, textiles and/or fabric, are selected from hexosaminidases from the *Terribacillus* clade. In one aspect the hexosaminidases is selected from any of the polypeptides having SEQ ID NOS 12, 13, 14, 19, 20 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. In one aspect, the hexosaminidase is a polypeptide with SEQ ID NO 12 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. In one aspect, the hexosaminidase is a polypeptide with SEQ ID NO 13 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. In one aspect, the hexosaminidase is a polypeptide with SEQ ID NO 14 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. In one aspect, the hexosaminidase is a polypeptide with SEQ ID NO 19 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto. In one aspect, the hexosaminidase is a polypeptide with SEQ ID NO 20 or polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity hereto.

Preferably the hexosaminidase is selected from the *Curtobacterium* clade or the *Terribacillus* clade, most preferably the hexosaminidase is selected from the *Terribacillus* clade.

The enzymes having DNase activity to be used in the cleaning composition of the invention, which are useful for deep cleaning of items such as hard surfaces, textiles and/or fabric, are preferably selected from DNase which is obtainable from a fungus. A DNase which is obtainable from an *Aspergillus* is preferred; a DNase which is obtainable from *Aspergillus oryzae* is preferred. In one embodiment of the present invention, the enzyme having deoxyribonuclease activity is not the S1 nuclease from *Aspergillus oryzae*.

The DNase used in the present invention preferably includes the polypeptide having SEQ ID NO: 2, which is obtained from *Aspergillus oryzae*. One aspect of the present invention relates to isolated enzymes having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and which have DNase activity.

Biofilm can develop on textile when microorganisms are present on an item and stick together on the item. This biofilm may adhere soil due to its sticky nature.

The present invention concerns the use of a cleaning composition comprising an enzyme having DNase activity and an enzyme having hexosaminidase activity for deep cleaning of an item, wherein the DNase is an enzyme having at least 60% sequence identity to the amino acid sequence having SEQ ID NO: 2, wherein the hexosaminidase is an enzyme having at least 60% sequence identity to the amino acid sequence having SEQ ID NO: 3, 4, 5, 6, 7, 8, 9, 10, 11, 12, 13, 14, 15, 16, 17, 18, 19 or 20 and wherein the item is a textile. In one aspect of the invention the cleaning composition is used for preventing, reducing or removing the stickiness of an item. The cleaning composition can further be used for pre-treating stains on textile such as textile with a pronounced amount of biofilm adhered to the textile.

Additionally, the invention concerns use of the cleaning composition for preventing, reducing or removing re-deposition of soil during a wash cycle. When the cleaning composition is used for example in the laundering of textile, the cleaning composition hinders deposition of soil present in the wash liquor on the textile.

Further, the invention concerns the use of a cleaning composition for preventing, reducing or removing the adherence of soil to an item. In one embodiment, the item is textile. When the soil does not adhere to the item, the item appears cleaner. Thus, the invention further concerns the use of a cleaning composition according to the invention for maintaining or improving the whiteness of the item.

When items like T-shirts or sportswear are used, they are exposed to bacteria from the body of the user and from the rest of the environment in which they are used. This may cause malodor on the item even after the item is washed. The present invention therefore also concerns removal or reduction of malodor on textile. The malodor may be caused by bacteria producing compounds with an unpleasant smell. One example of such unpleasant smelling compounds is E-2-nonenal. The malodor can be present on newly washed textile which is still wet, or the malodor can be present on newly washed textile which has subsequently been dried. The malodor may also be present on textile which has been stored for some time after wash. The present invention relates to reduction or removal of malodor such as E-2-nonenal from wet or dry textile.

The cleaning composition according to the invention may comprise a cleaning adjunct; the cleaning adjunct ingredient may be selected from surfactants and builders and/or chelators such as those described above. The adjunct ingredients may also be any of the following: a flocculating aid, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments.

In one embodiment, the cleaning adjunct ingredient is a builder or a clay soil removal/anti-redeposition agent.

In one embodiment, the cleaning adjunct ingredient is one or more enzymes. The one or more enzymes may be selected from the group consisting of proteases, lipases, cutinases, amylases, carbohydrases, cellulases, pectinases, mannanases, arabinases, galactanases, xylanases and oxidases.

In addition to the enzymes having DNase activity and the enzyme having hexosaminidase activity the detergents of the invention may further comprise cellulases. Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g., the fungal cellulases produced from *Humicola insolens*, *Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase polypeptides such as those described in WO 94/07998, EP 0 531 315, U.S. Pat. Nos. 5,457,046, 5,686,593, 5,763,254, WO 95/24471, WO 98/12307 and PCT/DK98/00299.

Examples of cellulases exhibiting endo-beta-1,4-glucanase activity (EC 3.2.1.4) are those described in WO02/099091.

Other examples of cellulases include the family 45 cellulases described in WO96/29397, and especially polypeptides thereof having substitution, insertion and/or deletion at one or more of the positions corresponding to the following positions in SEQ ID NO: 8 of WO 02/099091: 2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146R.

Commercially available cellulases include Celluzyme™, Celluclean and Carezyme™ (Novozymes NS), Clazinase™, and Puradax HA™ (Genencor International Inc.), and KAC-500(B)™ (Kao Corporation).

In addition to the enzymes having DNase activity and the enzyme having hexosaminidase activity the cleaning composition of the invention may further comprise proteases. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloprotease may for example be a thermolysin from e.g. family M4 or other metalloprotease such as those from the M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the *Bacillus lentus* protease shown in SEQ ID NO 1 of WO 2016/001449. More preferred the subtilase variants may comprise one or more of the mutations: S3T, V4I, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211D, N212D, N212S, M216S, A226V, K229L, Q230H, Q239R, N246K, N255W, N255D, N255E, L256E, L256D T268A, R269H, wherein the positions correspond to the positions of the *Bacillus lentus* protease shown in SEQ ID NO 1 of WO 2016/001449. The protease variants are preferably variants of the *Bacillus lentus* protease (Savinase®) shown in SEQ ID NO 1 of WO 2016/001449, the *Bacillus amylolichenifaciens* protease (BPN') shown in SEQ ID NO 2 of WO2016/001449. The protease variants preferably have at least 80% sequence identity to SEQ ID NO 1 or SEQ ID NO 2 of WO 2016/001449.

Another protease variant is one comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus subtilisin*) from Kao.

In addition to the enzymes having DNase activity and the enzyme having hexosaminidase activity the cleaning composition of the invention may further comprise lipases and cutinases which include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase polypeptides such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and polypeptides of the *M. smegmatis* perhydrolase in particular the S54V variant used in the commercial product Gentle Power Bleach from Huntsman Textile Effects Pte Ltd (WO10/100028).

In addition to the enzymes having DNase activity and the enzyme having hexosaminidase activity the cleaning composition of the invention may further comprise amylases. The amylase may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 3 in WO 95/10603 or polypeptides having 90% sequence identity to SEQ ID NO: 3 thereof. Preferred polypeptides are described in WO 94/02597, WO 94/18314, WO 97/43424 and SEQ ID NO: 4 of WO 99/019467, such as polypeptides with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or polypeptides thereof having 90% sequence identity to SEQ ID NO: 6. Preferred polypeptides of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or polypeptides having 90% sequence identity thereof. Preferred polypeptides of this hybrid alpha-amylase are those having a substitution, a deletion or an insertion in one or more of the following positions: G48, T49, G107, H156, A181, N190, M197, I201, A209 and Q264. Most preferred polypeptides of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or polypeptides thereof having 90% sequence identity to SEQ ID NO: 6. Preferred polypeptides of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or polypeptides thereof having 90% sequence identity to SEQ ID NO: 1, SEQ ID NO: 2, SEQ ID NO: 3 or SEQ ID NO: 7. Preferred polypeptides of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred polypeptides are those having a deletion in positions 181 and 182 or positions 183 and 184. Most preferred amylase polypeptides of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or polypeptides thereof having 90% sequence identity to SEQ ID NO: 2 of WO 08/153815 or 90% sequence identity to SEQ ID NO: 10 in WO 01/66712. Preferred polypeptides of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or polypeptides having 90% sequence identity to SEQ ID NO: 2 thereof. Preferred polypeptides of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred polypeptides of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase polypeptides of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K, wherein the polypeptides are C-terminally truncated and optionally further comprise a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase polypeptides are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include polypeptides having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase polypeptides such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes NS), and Rapidase™, Purastar™/Effectenz™, Powerase and Preferenz S100 (from Genencor International Inc./DuPont).

In addition to the enzymes having DNase activity and the enzyme having hexosaminidase activity the cleaning composition of the invention may further comprise peroxidases/oxidases including those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent or cleaning composition enzyme(s) may be included in a detergent composition by adding separate additives containing one or more enzymes, or by adding a combined additive comprising these enzymes. A detergent additive of the invention, i.e., a separate additive or a combined additive, can be formulated, for example, as a granulate, liquid, slurry, etc. Preferred detergent additive formulations are granulating, non-dusting granulates, liquids, stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly (ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The cleaning compositions of the invention may also contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), (carboxymethyl) inulin (CMI), and polycarboxylates such as PAA, PAA/ PMA, polyaspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/ reflection of visible light. Fluorescent whitening agents emit at least some visible light if subjected to ultraviolet light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/ 03276 and EP1876226 (hereby incorporated by reference). The cleaning composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/ 087243.

The cleaning may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The cleaning compositions of the present invention may also include one or more dye transfer inhibiting agents. Suitable polymeric dye transfer inhibiting agents include, but are not limited to, polyvinylpyrrolidone polymers, polyamine-N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The cleaning compositions of the present invention will preferably also contain additional components that may tint articles being cleaned, such as fluorescent whitening agents or optical brighteners. Where present the brightener is preferably at a level of about 0.01% to about 0.5% by weight. Any fluorescent whitening agent suitable for use in a laundry detergent composition may be used in the cleaning composition of the present invention. The most commonly used fluorescent whitening agents are those belonging to the classes of diaminostilbene-sulfonic acid derivatives, diarylpyrazoline derivatives and biphenyl-distyryl derivatives. Examples of the diaminostilbene-sulfonic acid derivative type of fluorescent whitening agents include the sodium salts of: 4,4'-bis[(4-anilino-6-diethanolamino-s-triazin-2-yl) amino]stilbene-2,2'-disulfonate, 4,4'-bis[(4,6-dianilino-s-triazin-2-yl)amino]stilbene-2,2'-disulfonate, 4,4'-bis{4-anilino-6-[methyl(2-hydroxyethyl)amino]-s-triazin-2-ylamino}stilbene-2,2'-disulfonate, 4,4'-bis(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl] benzenesulfonate. Preferred fluorescent whitening agents are Tinopal DMS and Tinopal CBS available from BASF. Tinopal DMS is the disodium salt of 4,4'-bis[(4-anilino-6-morpholino-s-triazin-2-yl) amino] stilbene-2,2'-disulfonate. Tinopal CBS is the disodium salt of 2,2'-[biphenyls-4,4'-di (2,1-ethenediyl)] dibenzene-1-sulfonate. Also preferred is the commercially available Parawhite KX, supplied by Paramount Minerals and Chemicals, Mumbai, India. Other fluorescers suitable for use include the 1-3-diarylpyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

The cleaning compositions of the present invention may also include one or more soil-release polymers which aid the removal of soils from fabrics such as cotton and polyester-based fabrics, the removal of hydrophobic soils from polyester-based fabrics. The soil release polymers may for example be nonionic or anionic terephthalate-based polymers, polyvinylcaprolactam and related copolymers, vinyl graft copolymers or polyester polyamides; see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil-release polymers. Suitable graft co-polymers are described in more detail in WO 2007/138054, WO 2006/108856 and WO 2006/113314 (hereby incorporated by reference). Other soil-release polymers are substituted polysaccharide structures especially substituted cellulosic structures such as modified cellulose derivatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof.

The cleaning compositions of the present invention may also include one or more anti-redeposition agents such as (carboxymethyl) cellulose (CMC), poly (vinyl alcohol) (PVA), homopolymers of acrylic acid, copolymers of acrylic acid and maleic acid, and ethoxylated polyethyleneimines. The cellulose based polymers described under soil-release polymers above may also function as anti-redeposition agents.

The cleaning composition of the invention may also contain one are more adjunct materials. Suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Cleaning Products

The cleaning composition of the invention, e.g. a detergent composition, may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids: US2009/0011970 A1.

Cleaning ingredients, such as detergent ingredients, can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent which is not unit dosed may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The enzyme having DNase activity and the enzyme having hexosaminidase activity may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix may be added to the soap at different stages of the process. For example, the premix containing a soap, enzymes of the invention, optionally one or more additional enzymes, a protease inhibitor, and a salt of a monovalent cation and an organic anion may be prepared and the mixture is then plodded. The enzymes of the invention and optional additional enzymes may be added at the same time as the protease inhibitor for example in liquid form. Besides the mixing step and the plodding step, the process may further comprise the steps of milling, extruding, cutting, stamping, cooling and/or wrapping.

Formulation of Enzyme in Co-Granule

The enzyme having DNase activity and the enzyme having hexosaminidase activity may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry are disclosed in the IP.com disclosure IPCOM000200739D.

Another example of formulation of enzymes using co-granulates is disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink components and the composition additionally comprises from 20 to 80 wt % detergent moisture sink components. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

The multi-enzyme co-granule may comprise a enzymes of the invention and (a) one or more enzymes selected from the group consisting of first-wash lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The invention is further summarized in the following paragraphs:

1. Use of a combination of an enzyme having DNase activity and an enzyme having hexosaminidase activity for deep cleaning of an item, wherein the item is a textile.
2. Use according to paragraph 1 for preventing, reducing or removing stickiness of the item.
3. Use according to any of paragraphs 1 or 2 for pre-treating stains on the item.
4. Use according to any of paragraphs 1-3 for preventing, reducing or removing re-deposition of soil during a wash cycle.
5. Use according to any of paragraphs 1-4 for preventing, reducing or removing adherence of soil to the item.
6. Use according to any of the preceding paragraphs for maintaining or improving the whiteness of the item.
7. Use according to any of the preceding paragraphs, wherein a malodor is reduced or removed from the item.
8. Use according to any of the preceding paragraphs, wherein the textile is made of cotton, Cotton/Polyester, Polyester, Polyamide, Polyacryl and/or silk.
9. Use of a combination of an enzyme having DNase activity and an enzyme having hexosaminidase activity for deep cleaning of an item, wherein the item is a hard surface.
10. Use according to any of the preceding paragraphs, wherein the enzyme having hexosaminidase activity is a dispersin.
11. Use according to any of the preceding paragraphs, wherein the enzyme having hexosaminidase activity is selected from the group consisting of DspB clade, the *Curtobacterium* clade and the *Terribacillus* clade.
12. Use according to any of paragraphs 10 or 11, wherein the enzyme having hexosaminidase activity is selected from the DspB clade.
13. Use according to paragraph 12, wherein the enzyme having hexosaminidase activity is selected from polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity the amino acid sequences with SEQ ID NOS 3, 4, 5, 6, 7, 8, 9, 10.
14. Use according to any of paragraphs 10 or 11, wherein the enzyme having hexosaminidase activity is selected from the *Curtobacterium* clade.
15. Use according to paragraph 14, wherein the enzyme having hexosaminidase activity is a polypeptide having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence with SEQ ID NO 11, 15, 16, 17 or 18.

16. Use according to any of paragraphs 10 or 11, wherein the enzyme having hexosaminidase activity is selected from the *Terribacillus* clade.
17. Use according to paragraph 16, wherein the enzyme having hexosaminidase activity is selected from polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity the amino acid sequences with SEQ ID NO 12, 13, 14, 19 or 20.
18. Use according to any of the preceding claims, wherein the enzyme having DNase activity is a fungal DNase.
19. Use according to paragraph 18, wherein the enzyme having DNase activity is obtained from *Aspergillus*.
20. Use according to paragraph 19, wherein the enzyme having DNase activity is obtained from *Aspergillus oryzae*.
21. Use according to any of the paragraphs 18 to 20, wherein the enzyme having DNase activity is a polypeptide having a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.
22. A composition comprising an enzyme having DNase activity and an enzyme having hexosaminidase activity and an adjunct ingredient, such as a cleaning agent.
23. The composition according to paragraph 22, wherein the adjunct ingredient is selected from the group consisting of surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
24. The composition according to any of the preceding composition paragraphs wherein the composition comprises from about 2 wt % to about 50 wt %, 5 wt % to about 50 wt %, from about 5 wt % to about 40 wt %, from about 5 wt % to about 30 wt %, from about 5 wt % to about 20 wt %, from about 5 wt % to about 10 wt % anionic surfactant, preferably selected from linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.
25. The composition according to any of the preceding composition paragraphs wherein the composition comprises from about 2 wt % to about 50 wt %, 5 wt % to about 50 wt %, 10 wt % to about 50 wt % of at least one builder, preferably selected from citric acid, methylglycine-N, N-diacetic acid (MGDA) and/or glutamic acid-N, N-diacetic acid (GLDA) and mixtures thereof.
26. The composition according to any of the preceding composition paragraphs wherein the composition comprises at least one bleach component, preferably a percarbonate and a manganese catalyst, preferably 1,4,7-trimethyl-1,4,7-triazacyclononane or manganese (III) acetate tetrahydrate (MnTACN).
27. The composition according to any of the preceding paragraphs, wherein the enzyme having hexosaminidase activity is a dispersin.
28. The composition according to any of the preceding paragraphs, wherein the enzyme having hexosaminidase activity is selected from the group consisting of DspB clade, the *Curtobacterium* clade and the *Terribacillus* clade.
29. The composition according to any of paragraphs 27 or 28, wherein the enzyme having hexosaminidase activity is selected from the DspB clade.
30. The composition according to paragraph 29, wherein the enzyme having hexosaminidase activity is selected from polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity the amino acid sequences with SEQ ID NOS 3, 4, 5, 6, 7, 8, 9 and 10.
31. The composition according to any of paragraphs 27 or 28, wherein the enzyme having hexosaminidase activity is selected from the *Curtobacterium* clade.
32. The composition according to paragraph 31, wherein the enzyme having hexosaminidase activity is a polypeptide having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequence with SEQ ID NO 11, 15, 16, 17 or 18.
33. The composition according to any of paragraphs 27 or 28, wherein the enzyme having hexosaminidase activity is selected from the *Terribacillus* clade.
34. The composition according to paragraph 33, wherein the enzyme having hexosaminidase activity is selected from polypeptides having at least 60%, such as at least 65%, such as at least 70%, such as at least 75%, such as at least 80%, such as at least 85%, or such as at least 90%, such as at least 91%, such as at least 92%, such as at least 93%, such as at least 94%, such as at least 95%, such as at least 96%, such as at least 97%, such as at least 98%, such as at least 99% or 100% sequence identity to the amino acid sequences with SEQ ID NOS 12, 13, 14, 19 or 20.
35. The composition according to any of the preceding claims, wherein the enzyme having DNase activity is a fungal DNase.
36. The composition according to paragraph 35, wherein the enzyme having DNase activity is obtained from *Aspergillus*.

37. The composition according to paragraph 36, wherein the enzyme having DNase activity is obtained from *Aspergillus oryzae*.
38. The composition according to any of the paragraphs 35 to 37, wherein the enzyme having DNase activity is a polypeptide having a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.
39. The composition according to any of the preceding paragraphs comprising from about 5 wt % to about 40 wt % nonionic surfactants, and from about 0 wt % to about 50 wt % anionic surfactants.
40. The composition according to paragraph 39, wherein the nonionic surfactant is selected from alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA) and combinations thereof.
41. The composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.
42. The composition according to any of the preceding composition paragraphs, wherein the enzyme is a protease, which is of animal, vegetable or microbial origin.
43. The composition according to any of the preceding composition paragraphs, wherein the protease is chemically modified or protein engineered.
44. The composition according to any of the preceding composition paragraphs, wherein the protease is a serine protease or a metalloprotease, preferably an alkaline microbial protease or a trypsin-like protease.
45. The composition according to any of the preceding composition paragraphs, wherein the protease is selected from the group consisting of *Bacillus*, e.g., subtilisin Novo, subtilisin Carlsberg, subtilisin 309, subtilisin 147, subtilisin 168, trypsin of bovine origin, trypsin of porcine origin and *Fusarium* protease.
46. The composition according to any of the preceding composition paragraphs, wherein the biofilm comprising components such as DNA or PNAG is produced by any of the following; *Acinetobacter* sp., *Aeromicrobium* sp., *Brevundimonas* sp., *Microbacterium* sp., *Micrococcus luteus*, *Pseudomonas* sp., *Staphylococcus* sp., and *Stenotrophomonas* sp. particularly, *Bacillus subtillis, Escherichia coli, Staphylococcus aureus, Staphylococcus epidermidis, Pseudomonas fluorescens, Yersinia pestis, Aggregatibacter actinomycetemcomitans, Streptococcus pyogenes, Streptococcus dysgalactiae* (group C strep), *Enterococcus faecalis, Listeria monocytogenes, Clostridium difficile, Mycobacterium tuberculosis, Mycobacterium smegmatis; Neisseria meningitides, Neisseria gonorrhea*, nontypable *Haemophilus influenzae, Haemophilus ducreyi, Helicobacter pylon, Campylobacter jejuni; Citrobacter rodentium, Salmonella enterica serovars typhi, Salmonella typhimurium, Candida albicans, Aspergillus flavus, Fusarium solani*, and *Cryptococcus neoformans, Acinetobacter baumannii, Actinobacillus actinomycetemcomitans, Bdellovibrio bacterivorous, Bordetella pertussis, Bordetella bronchiectasis, Campylobacter jejuni, Comamonas denitrificans, Escherichia coli, Haemophilus influenza, Klebsiella pneumoniae, Neisseria meningitides, Pseudomonas aeruginosa, Shewanella oneidensis, Vibrio cholera*, Gram-positive bacteria, *Bacillus licheniformis, Bacillus subtilis, Enterococcus faecalis, Listeria monocytogenes, Micrococcus luteus, Staphylococcus aureus, Staphylococcus epidermidis, Staphylococcus haemolyticus, Streptococcus anginosus, Streptococcus constellatus, Streptococcus salivarius, Staphylococcus lugdunesis, Streptococcus intermedius, Streptococcus intermedius, Streptococcus mutans, Streptococcus pneumoniae, Streptococcus pyogenes, Aspergillus fumigatus* and *Candida albicans*
47. The composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.
48. The composition according to any of the preceding composition paragraphs, wherein the composition is a cleaning composition selected from liquid detergent, powder detergent and granule detergent compositions.
49. A method for laundering an item comprising the steps of:
    a) Exposing an item to a wash liquor comprising an enzyme having DNase activity and enzyme having hexosaminidase activity or a composition according to any of paragraphs 22-48;
    b) Completing at least one wash cycle; and
    c) Optionally rinsing the item,
    wherein the item is a textile.
50. Method according to paragraph 49, wherein the pH of the wash liquor is in the range of 1 to 11.
51. Method according to any of the preceding method paragraphs, wherein the pH of the wash liquor is in the range 5.5 to 11, such as in the range of 7 to 9, in the range of 7 to 8 or in the range of 7 to 8.5.
52. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C., in the range of 20° C. to 40° C., in the range of 15° C. to 30° C. or in the range of 20° C. to 30° C.
53. Method according to any of the preceding method paragraphs, wherein the temperature of the wash liquor is from about 20° C. to about 40° C.
54. Method according to any of the preceding method paragraphs, wherein the temperature of the wash liquor is from about 15° C. to about 30° C.
55. Method according to any of the preceding method paragraphs, wherein stains present on the item is pretreated with an enzyme having DNase activity and an enzyme having hexosaminidase activity or a detergent composition according to any of paragraphs 22-48.
56. Method according to any of the preceding method paragraphs, wherein stickiness of the item is reduced.
57. Method according to any of the preceding method paragraphs, wherein redeposition of soil is reduced.

58. Method according to any of the preceding method paragraphs, wherein adherence of soil to the item is reduced or removed.
59. Method according to any of the preceding method paragraphs, wherein whiteness of the item is maintained or improved.
60. Method according to any of the preceding method paragraphs, wherein malodor is reduced or removed from the item.
61. Method according to any of the preceding method paragraphs, wherein the concentration of DNase in the wash liquor is preferably at least at least 0.00001 mg/L or at least 0.0001 or at least 0.001 mg/L of enzyme or at least 0.01, 0.02, 0.05, 0.1, 0.2, 0.5, 1, 2, 5, 10 or at least 15 µg active enzyme per liter of wash liquor, optionally the concentration of enzyme in the wash liquor is in the range of about 0.00002 mg/L to about 2 mg/L, about 0.0002 mg/L to about 2 mg/L, about 0.002 mg/L to about 2 mg/L, such as about 0.02 mg/L to about 2 mg/L, such as about 0.2 mg/L to about 2 mg/L or in the range of about 0.00001 mg/L to about 1 mg/L, about 0.0001 mg/L to about 1 mg/L, about 0.0001 mg/L to about 10 mg/L or in the range of in the range of about 0.001 mg/L to about 10 mg/L, or in the range of about 0.01 mg/L to about 10 mg/L, or in in the range of about 0.1 mg/L to about 10 mg/L per liter of wash liquor, and optionally weight percent of composition of the DNase is present in an amount corresponding to at least 0.0001 wt %, at least 0.0002 wt %, at least 0.0005 wt %, preferably at least 0.001 wt %, preferably at least 0.002 wt %, preferably at least 0.005 wt %, preferably at least 0.01 wt %, preferably at least 0.02 wt %, preferably at least 0.05 wt % preferably at least 0.1 wt % of the total detergent concentration, the concentration of DNase is preferably within the ranges from about 0.0001 wt % to about 10 wt %, such as from about 0.0001 wt % to about 5 wt %, such as from about 0.0002 wt % to about 5 wt %, such as from about 0.001 wt % to about 1 wt %, such as from about 0.005 wt % to about 1 wt %, such as from about 0.01 wt % to about 1 wt %, such as from about 0.01 wt % to about 0.5 wt % or most preferred from about 0.002 wt % to about 0.01 wt % active enzyme in the total detergent concentration.
62. Method according to any of the preceding method paragraphs, wherein the concentration of the polypeptide having hexosaminidase activity in the wash liquor is preferably at least at least 0.00001 mg/L or at least 0.0001 or at least 0.001 mg/L of enzyme or at least 0.01, 0.02, 0.05, 0.1, 0.2, 0.5, 1, 2, 5, 10 or at least 15 µg active enzyme per liter of wash liquor, optionally the concentration of enzyme in the wash liquor is in the range of about 0.00002 mg/L to about 2 mg/L, about 0.0002 mg/L to about 2 mg/L, about 0.002 mg/L to about 2 mg/L, such as about 0.02 mg/L to about 2 mg/L, such as about 0.2 mg/L to about 2 mg/L or in the range of about 0.00001 mg/L to about 1 mg/L, about 0.0001 mg/L to about 1 mg/L, about 0.0001 mg/L to about 10 mg/L or in the range of in the range of about 0.001 mg/L to about 10 mg/L, or in the range of about 0.01 mg/L to about 10 mg/L, or in in the range of about 0.1 mg/L to about 10 mg/L per liter of wash liquor and optionally weight percent of the hexosaminidase of the composition at least 0.0001 wt %, preferably at least 0.001 wt %, preferably at least 0.002 wt %, preferably at least 0.005 wt %, preferably at least 0.01 wt %, preferably at least 0.02 wt %, preferably at least 0.05 wt % preferably at least 0.1 wt % of the total detergent concentration, preferably within the ranges from about 0.0001 wt % to about 10 wt %, such as from about 0.001 wt % to about 0.1 wt %, such as from about 0.005 wt % to about 0.1 wt %, such as from about 0.01 wt % to about 0.1 wt %, such as from about 0.01 wt % to about 0.5 wt % or most preferred from about 0.002 wt % to about 0.01 wt % active enzyme in the total detergent concentration
63. Item laundered according to the method of any of paragraphs 49-62.

Every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Assays and Detergent Compositions
Detergent Compositions
The below mentioned detergent compositions may be used in combination with the enzyme of the invention.
Biotex Black (Liquid)
5-15% Anionic surfactants, <5% Nonionic surfactants, perfume, enzymes, DMDM and hydantoin.
Composition of Ariel Sensitive White & Color, Liquid Detergent Composition
Aqua, Alcohol Ethoxy Sulfate, Alcohol Ethoxylate, Amino Oxide, Citric Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).
Composition of WFK IEC-A Model Detergent (Powder)
Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.
Composition of Model Detergent A (Liquid)
Ingredients: 12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (all percentages are w/w)
Composition of Ariel Actilift (Liquid)
Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.
Composition of Ariel Actilift Colour&Style (Liquid)
Ingredients: 5-15% Anionic surfactants; <5% Non-ionic surfactants, Phosphonates, Soap; Enzymes, Perfumes, Benzisothiazolinone, Methylisothiazolinone, Alpha-isomethyl ionone, Butylphenyl methylpropional, Citronellol, Geraniol, Linalool.
Composition of Persil Small & Mighty (Liquid)
Ingredients: 15-30% Anionic surfactants, Non-ionic surfacts, 5-15% Soap, <5% Polycarboxylates, Perfume, Phosphates, Optical Brighteners Persil 2 in 1 with Comfort Passion Flower Powder Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Stearic Acid, Parfum, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Alpha-Isomethyl Ionone, Disodium Distyrylbiphenyl Disulfonate, Cellulose, Protease, Limonene, PEG-75, Titanium dioxide, Dextrin, Sucrose, Sodium Polyaryl Sulphonate, CI 12490, CI 45100, CI 42090, Sodium Thiosulfate, CI 61585.

Persil Biological Powder

Sucrose, Sorbitol, Aluminum Silicate, Polyoxymethylene Melamine, Sodium Polyaryl Sulphonate, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Biological Tablets

Sodium carbonate, Sodium Carbonate Peroxide, Sodium bicarbonate, Zeolite, Aqua, Sodium Silicate, Sodium Lauryl Sulfate, Cellulose, TAED, Sodium Dodecylbenzenesulfonate, Hemicellulose, Lignin, Lauryl Glucoside, Sodium Acrylic Acid/MA Copolymer, Bentonite, Sodium chloride, Parfum, Tetrasodium Etidronate, Sodium sulfate, Sodium Polyacrylate, Dimethicone, Disodium Anilinomorpholinotriazinylaminostilbenesulfonate, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, CI 12490, Sodium Polyaryl Sulphonate, Sodium Thiosulfate, Amylase, Kaolin, Persil Colour Care Biological Powder Subtilisin, Imidazolidinone, Hexyl Cinnamal, Sucrose, Sorbitol, Aluminum Silicate, Polyoxymethylene Melamine, CI 61585, CI 45100, Lipase, Amylase, Xanthan gum, Hydroxypropyl methyl cellulose, CI 12490, Disodium Distyrylbiphenyl Disulfonate, Sodium Thiosulfate, CI 42090, Mannanase, CI 11680, Etidronic Acid, Tetrasodium EDTA.

Persil Colour Care Biological Tablets

Sodium bicarbonate, Sodium carbonate, Zeolite, Aqua, Sodium Silicate, Sodium Lauryl Sulfate, Cellulose Gum, Sodium Dodecylbenzenesulfonate, Lauryl Glucoside, Sodium chloride, Sodium Acrylic Acid/MA Copolymer, Parfum, Sodium Thioglycolate, PVP, Sodium sulfate, Tetrasodium Etidronate, Sodium Polyacrylate, Dimethicone, Bentonite, Dodecylbenzene Sulfonic Acid, Trimethylsiloxysilicate, Calcium carbonate, Cellulose, PEG-75, Titanium dioxide, Dextrin, Protease, Corn Starch Modified, Sucrose, Sodium Thiosulfate, Amylase, CI 74160, Kaolin.

Persil Dual Action Capsules Bio

MEA-Dodecylbenzenesulfonate, MEA-Hydrogenated Cocoate, C12-15 Pareth-7, Dipropylene Glycol, Aqua, Tetrasodium Etidronate, Polyvinyl Alcohol, Glycerin, Aziridine, homopolymer ethoxylated, Propylene glycol, Parfum, Sodium Diethylenetriamine Pentamethylene Phosphonate, Sorbitol, MEA-Sulfate, Ethanolamine, Subtilisin, Glycol, Butylphenyl Methylpropional, Boronic acid, (4-formylphenyl), Hexyl Cinnamal, Limonene, Linalool, Disodium Distyrylbiphenyl Disulfonate, Alpha-Isomethyl Ionone, Geraniol, Amylase, Polymeric Blue Colourant, Polymeric Yellow Colourant, Talc, Sodium chloride, Benzisothiazolinone, Mannanase, Denatonium Benzoate.

Persil 2 in 1 with Comfort Sunshiny Days Powder

Sodium sulfate, Sodium carbonate, Sodium Dodecylbenzenesulfonate, Bentonite, Sodium Carbonate Peroxide, Sodium Silicate, Zeolite, Aqua, Citric acid, TAED, C12-15 Pareth-7, Parfum, Stearic Acid, Sodium Acrylic Acid/MA Copolymer, Cellulose Gum, Corn Starch Modified, Sodium chloride, Tetrasodium Etidronate, Calcium Sodium EDTMP, Disodium Anilinomorpholinotriazinylaminostilbenesulfonate, Sodium bicarbonate, Phenylpropyl Ethyl Methicone, Butylphenyl Methylpropional, Glyceryl Stearates, Calcium carbonate, Sodium Polyacrylate, Geraniol, Disodium Distyrylbiphenyl Disulfonate, Cellulose, Protease, PEG-75, Titanium dioxide, Dextrin, Sucrose, Sodium Polyaryl Sulphonate, CI 12490, CI 45100, CI 42090, Sodium Thiosulfate, CI 61585.

Persil Small & Mighty 2in1 with Comfort Sunshiny Days

Aqua, C12-15 Pareth-7, Sodium Dodecylbenzenesulfonate, Propylene glycol, Sodium Hydrogenated Cocoate, Triethanolamine, Glycerin, TEA-Hydrogenated Cocoate, Parfum, Sodium chloride, Polyquaternium-10, PVP, Polymeric Pink Colourant, Sodium sulfate, Disodium Distyrylbiphenyl Disulfonate, Butylphenyl Methylpropional, Styrene/Acrylates Copolymer, Hexyl Cinnamal, Citronellol, Eugenol, Polyvinyl Alcohol, Sodium acetate, Isopropyl alcohol, Polymeric Yellow Colourant, Sodium Lauryl Sulfate.

Persil Small & Mighty Bio

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Disodium Distyrylbiphenyl Disulfonate, Butylphenyl Methylpropional, Styrene/Acrylates Copolymer, Citronellol, Sodium sulfate, Peptides, salts, sugars from fermentation (process), Subtilisin, Glycerin, Boronic acid, (4-formylphenyl), Geraniol, Pectate Lyase, Amylase, Sodium Lauryl Sulfate, Mannanase, CI 42051.

Persil Small & Mighty Capsules Biological

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, Sorbitol, MEA-Sulfate, Ethanolamine, Subtilisin, Glycol, Butylphenyl Methylpropional, Hexyl Cinnamal, Starch, Boronic acid, (4-formylphenyl), Limonene, Linalool, Disodium Distyrylbiphenyl Disulfonate, Alpha-Isomethyl Ionone, Geraniol, Amylase, Talc, Polymeric Blue Colourant, Sodium chloride, Benzisothiazolinone, Denatonium Benzoate, Polymeric Yellow Colourant, Mannanase.

Persil Small & Mighty Capsules Colour Care

MEA-Dodecylbenzenesulfonate, MEA-Hydrogenated Cocoate, C12-15 Pareth-7, Dipropylene Glycol, Aqua, Glycerin, Polyvinyl Alcohol, Parfum, Aziridine homopolymer ethoxylated, Sodium Diethylenetriamine Pentamethylene Phosphonate, Propylene glycol, MEA-Sulfate, Ethanolamine, PVP, Sorbitol, Butylphenyl Methylpropional, Subtilisin, Hexyl Cinnamal, Starch, Limonene, Linalool, Boronic acid, (4-formylphenyl), Alpha-Isomethyl Ionone, Geraniol, Talc, Polymeric Blue Colourant, Denatonium Benzoate, Polymeric Yellow Colourant.

Persil Small & Mighty Colour Care

Aqua, MEA-Dodecylbenzenesulfonate, Propylene glycol, Sodium Laureth Sulfate, C12-15 Pareth-7, TEA-Hydrogenated Cocoate, MEA-Citrate, Aziridine homopolymer ethoxylated, MEA-Etidronate, Triethanolamine, Parfum, Acrylates Copolymer, Sorbitol, MEA-Sulfate, Sodium Sulfite, Glycerin, Butylphenyl Methylpropional, Citronellol, Sodium sulfate, Peptides, salts, sugars from fermentation (process), Styrene/Acrylates Copolymer, Subtilisin, Boronic acid, (4-formylphenyl), Geraniol, Pectate Lyase, Amylase, Sodium Lauryl Sulfate, Mannanase, CI 61585, CI 45100.

Composition of Fairy Non-Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift Colour&Style (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Ariel Actilift (Powder)

Ingredients: 5-15% Anionic surfactants, Oxygen-based bleaching agents, <5% Non-ionic surfactants, Phosphonates, Polycarboxylates, Zeolites, Optical brighteners, Enzymes, Perfumes, Butylphenyl Methylpropional, Coumarin, Hexyl Cinnamal Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol sulfate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:

Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:

Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:
Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:
Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:
Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:
Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:
Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:
Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre-Treater Spray:
Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:
Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:
Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:
Polyvinyl Alcohol pouch film, wherein there is packed a liquid part and a powder part:
Liquid Ingredients: Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:
Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:
Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:
Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:
Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:
Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:
Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (high Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Wash Assays

Mini Launder-O-Meter (MiniLOM) Model Wash System

MiniLOM is a mini wash system in which washes are performed in 50 ml test tubes placed in a Stuart rotator. Each tube simulates one small washing machine and during an experiment, each will contain a solution of a specific detergent/enzyme system to be tested along with the soiled and unsoiled fabrics it is tested on. Mechanical stress is achieved via rotation (typically 20 rpm), and the temperature is controlled by placement of the rotator in a heating cabinet/room.

EXAMPLES

Assay I: Testing of Hexosaminidase Activity

The hexosaminidase activity of the polypeptides listed in the table below was determined using 4-nitrophenyl N-acetyl-β-D-glucosaminide (Sigma-Aldrich) as substrate. The enzymatic reaction was performed in triplicate in a 96 well flat bottom polystyrene microtiter plate (Thermo Scientific) with the following conditions: 50 mM 2-(N-morpholino) ethanesulfonic acid pH 6 buffer, 1.5 mg/ml 4-nitrophenyl N-acetyl-β-D-glucosaminide and 10, 20 or 50 µg/ml purified enzyme sample in a total reaction volume of 100 µl. Blank samples without polypeptide were run in parallel. The reactions were carried out at 37° C. in a Thermomixer comfort (Eppendorf). After 10 minutes of incubation, 5 µl 1 M NaOH was added to each reaction mixture to stop the enzymatic reaction. The absorbance was read at 405 nm using a POLARstar Omega plate reader (BMG LABTECH) to estimate the formation of 4-nitrophenolate ion released because of enzymatic hydrolysis of the 4-nitrophenyl N-acetyl-β-D-glucosaminide substrate. The results are summarized in table 1 below. The table shows the average absorbance measured at 405 nm for each reaction performed in triplicate. It is seen that the absorbance is higher for the reaction carried out with all the polypeptides listed in the table below compared to blank without polypeptide which demonstrates that all the tested polypeptides exhibit hexosaminidase activity.

TABLE 1

| Hexosaminidase activity. | | | |
|---|---|---|---|
| Enzyme | Enzyme concentration | A405 nm | ΔA405 nm (A405 nm$_{sample}$ − A405 nm$_{blank}$) |
| Blank | 0 µg/ml | 0.158 | — |
| SEQ ID NO 3 | 10 µg/ml | 1.352 | 1.194 |
| SEQ ID NO 4 | 10 µg/ml | 1.161 | 1.003 |
| SEQ ID NO 5 | 10 µg/ml | 0.332 | 0.174 |
| SEQ ID NO 6 | 10 µg/ml | 0.321 | 0.163 |
| SEQ ID NO 7 | 10 µg/ml | 2.903 | 2.745 |

TABLE 1-continued

Hexosaminidase activity.

| Enzyme | Enzyme concentration | A405 nm | ΔA405 nm (A405 nm$_{sample}$ − A405 nm$_{blank}$) |
|---|---|---|---|
| SEQ ID NO 8 | 10 µg/ml | 0.582 | 0.424 |
| SEQ ID NO 9 | 10 µg/ml | 0.938 | 0.780 |
| SEQ ID NO 10 | 10 µg/ml | 1.152 | 0.994 |
| SEQ ID NO 11 | 20 µg/ml | 0.376 | 0.197 |
| SEQ ID NO 12 | 50 µg/ml | 1.978 | 1.820 |
| SEQ ID NO 13 | 50 µg/ml | 1.715 | 1.557 |
| SEQ ID NO 14 | 50 µg/ml | 2.455 | 2.297 |

Assay II

Testing of DNase Activity

DNase activity was determined on DNase Test Agar with Methyl Green (BD, Franklin Lakes, N.J., USA), which was prepared according to the manual from the supplier. Briefly, 21 g of agar was dissolved in 500 ml water and then autoclaved for 15 min at 121° C. Autoclaved agar was temperated to 48° C. in a water bath, and 20 ml of agar was poured into petridishes and allowed to solidify by incubation overnight at room temperature. On solidified agar plates, 5 µl of enzyme solutions are added, and DNase activity is observed as colorless zones around the spotted enzyme solutions.

Assay IIa

DNase activity was determined by fluorescence using fluorescence-quenched DNA oligonucleotide probe. This probe emits signal after nuclease degradation according to the manual from the supplier (DNase alert kit, Integrated DNA Technology, Coralville, Iowa, USA). Briefly, 5 µl of the substrate was added to 95 µl of DNase. If the signal was too high, further dilutions of DNase was done in the adequate buffer. Kinetic curve was measured for 20 min at 22° C. using a Clariostar microplate reader (536 nm excitation, 556 nm emission).

Assay III

Wash performance is expressed as a delta remission value (ΔRem). After washing and rinsing the swatches were spread out flat and allowed to air dry at room temperature overnight. All washes are evaluated the day after the wash. Light reflectance evaluations of the swatches were done using a Macbeth Color Eye 7000 reflectance spectrophotometer with very small aperture. The measurements were made without UV in the incident light and remission at 460 nm was extracted. Measurements were made on unwashed and washed swatches. The test swatch to be measured was placed on top of another swatch of same type and color (twin swatch). With only one swatch of each kind per beaker, a swatch from a replicate wash was used in this way. Remission values for individual swatches were calculated by subtracting the remission value of the unwashed swatch from the remission value of the washed swatch. The total wash performance for each stained swatch set was calculated as the sum of individual ΔRem.

Calculating the enzyme effect is done by taking the measurements from washed swatches with enzymes and subtracting with the measurements from washed swatches without enzyme for each stain. The total enzyme performance is calculated as the sum of individual ΔRem$_{enzyme}$.

Example 1

Extraction of EPS (Extracellular Polymeric Substances) from *Pseudomonas fluorescens*

A *Pseudomonas fluorescens* isolate from Iceland was used as a model microorganism in the present example. *Pseudomonas fluorescens* was restreaked on Tryptone Soya Agar (TSA) (pH 7.3) (CM0131; Oxoid Ltd, Basingstoke, UK) and incubated for 1 day at 23° C. The strain was inoculated into 10 mL of TSB and the culture was incubated with shaking for 16 hours at 23° C. The overnight culture was diluted (1:100) in 200 ml M63 supplemented medium (15 mM $(NH_4)_2SO_4$, 100 mM $KH_2PO_4$, 1.8 µM $FeSO_4$, 1 mM $MgSO_4 \cdot 7H_2O$, 0.4% (w/v) glycerol, 0.2% (w/v) Casamino acids and 0.0001% (w/v) Thiamine) added to a Corning® CellBIND® 225 cm$^2$ Angled Neck Cell Culture Flask with Vent Cap and incubated statically for 5 days at 23° C. The biofilm culture was subsequently transferred to four 50 ml Falcon tubes and pelleted by centrifugation (10 min, 8000 g, 25° C.), and the supernatants were discarded completely. The residual pellets from each Falcon tube were resuspended in 0.450 ml 3M NaCl to extract the surface-associated EPS (extracellular polymeric substances) and pooled in one test tube (5 ml, Eppendorf). The suspension was centrifuged at 5000 g for 10 min at 25° C. and the 1.8 ml supernatant was transferred to a new test tube as EPS fraction and stored at −20° C. until further use (termed crude EPS).

Fluorescent Assay with WGA-Alexa Fluor® 488

50 ul aliquots of the crude EPS were spotted on two wells of a Nunc microtiter plate and incubated at room temperature for 45 min. Supernatant was then removed and 50 ul of PBS buffer was added to one well and 50 ul containing 20 ppm of enzyme (SEQ ID NO 14) was added to the other well. The plate was incubated 1 hour at 30° C. Next, supernatants were removed and 50 ul of 10 ug/ml of wheat germ agglutinin WGA-Alexa fluor488 fluorescent conjugate (Thermo Fischer Scientific, #W11261) was added to the wells. Alexa Fluor® 488 WGA binds to sialic acid and N-acetylglucosaminyl residues. The plate was incubated at room temperature for 15 min. Samples were washed with 50 ul water and the fluorescence at $\square_{excitation}$=495 nm and $\square_{emission}$=520 nm was measured with a SpectraMax M3 plate reader instrument. The measurements obtained are listed below in table 2.

TABLE 2

Fluorescent measurements of crude EPS from *P. fluorescence* treated with or without hexosaminidase (SEQ ID NO 14) stained with WGA-Alexa Fluor488 dye.

| Treatment | *P. fluorescens* EPS |
|---|---|
| control PBS | 122.724 |
| hexosaminidase (SEQ ID NO 14) | 13.361 |

Results from the fluorescent measurements show that the crude EPS sample from *P. fluorescence* is stained with WGA-Alexa Fluor488 suggesting that it contains poly N-acetyl-glucosamine (PNAG) and is sensitive to hexosaminidase hydrolysis.

DNA Content Analysis by Agarose Gel Electrophoresis 10 ul aliquot of the crude EPS was treated with and without DNase (2 ppm, SEQ ID NO 2) and subsequently subjected to agarose gel electrophoresis. The gel was stained with SyBrSafe (Invitrogen). In the EPS sample, a prominent band with a high molecular mass was detected in the 1% agarose gel corresponding to DNA. In contrast, in the EPS sample treated with DNase a prominent band with a small molecular mass was detected corresponding to small degradation fragments of DNA. The present study indicates that the crude EPS sample from *P. fluorescens* contained DNA and that it was degraded by DNase treatment.

Example 2

Synergistic Effect Between Hexosaminidase and DNase on Deep-Cleaning in Liquid Model Detergent 50 ul aliquots of the crude EPS described in Example 1 were spotted on sterile textile swatches (WFK20A) and incubated for 30 min at ambient temperature. The swatches (sterile or with EPS) were placed in 50 mL test tubes and 10 mL of wash liquor (15° dH water with 0.2 g/L iron(III) oxide nanopowder (544884; Sigma-Aldrich) with 3.33 g/L liquid model A detergent) and 0.2 ug/ml enzyme(s) was added to each tube. Washes without enzyme were included as controls. The test tubes were placed in a Stuart rotator and incubated for 1 hour at 37° C. at 20 rpm. The wash liquor was then removed, and the swatches were rinsed twice with 15° dH water and dried on filter paper over night. The remission ($REM^{460\ nm}$) values were measured using a Macbeth Color-Eye 7000 (CE7000), and are displayed in table 3. Delta values ($REM^{460\ nm}$ (swatch washed with enzyme)–$REM^{460\ nm}$ (swatch washed without enzyme)) are also indicated.

TABLE 3

Synergistic effect between hexosaminidase with SEQ ID NO 14 and DNase with SEQ ID NO 2 in deep-cleaning in model A detergent.

| Enzyme | Enzyme concentration (µg/ml) | $REM^{460\ nm}$ values | $\Delta REM^{460\ nm}$ ($REM^{460\ nm}_{with\ enzyme}$ – $REM^{460\ nm}_{without\ enzyme}$) |
|---|---|---|---|
| EPS, No enzyme | 0 | 40.3 | |
| EPS, hexosaminidase (SEQ ID NO 14) | 0.2 | 54.3 | 14.1 |
| EPS, DNase (SEQ ID NO 2) | 0.2 | 55.6 | 15.4 |
| EPS, hexosaminidase (SEQ ID NO 14) + DNase (SEQ ID NO 2) | 0.2 + 0.2 | 75.5 | 35.2 |

As seen in table 3, the wash performance of the enzyme cocktail comprising hexosaminidase (SEQ ID NO 14) and DNase (SEQ ID NO 2) (ΔREM460 nm (cocktail)=35.2) significantly exceeds the sum of the performances seen for of the individual enzymes (ΔREM460 nm (sum of individual enzyme treatments)=29.5), showing a synergetic effect between the enzymes. This also suggests that the different EPS components targeted by these enzymes are part of complex macromolecular structures, which shield other matrix components from enzymatic hydrolysis.

Example 3

Synergistic Effect Between Hexosaminidase and DNase on Deep-Cleaning in Liquid Model Detergent A *Pseudomonas fluorescens* isolate from Iceland was used as a model microorganism in the present example. *Pseudomonas fluorescens* was restreaked on Tryptone Soya Agar (TSA) (pH 7.3) (CM0131; Oxoid Ltd, Basingstoke, UK) and incubated for 1 day at 23° C. A single colony was inoculated into 10 mL of TSB and the culture was incubated for 16 hours at 23° C. with shaking (Tetramax 1000 at 460 rpm). After propagation, the culture was diluted to an OD600 of 0.03 in fresh TSB and 1.65 mL aliquots were added to the wells of 12-well polystyrene flat-bottom microplates (3512; Costar, Corning Incorporated, Corning, N.Y., USA), in which round swatches (diameter 2 cm) of sterile textile (WFK20A) had been placed. Sterile TSB was added to control wells. After 48 h at 23° C. (static incubation), the swatches were rinsed twice with 0.9% (w/v) NaCl.

Five rinsed swatches (sterile or with *P. fluourescens*) were placed in 50 mL test tubes and 10 mL of wash liquor (15° dH water with 0.2 g/L iron(III) oxide nanopowder (544884; Sigma-Aldrich) with 3.33 g/L liquid model A detergent) and 0.2 ppm enzymes was added to each tube. Washes without enzyme were included as controls. The test tubes were placed in a Stuart rotator and incubated for 1 hour at 30° C. at 20 rpm. The wash liquor was then removed, and the swatches were rinsed twice with 15° dH water and dried on filter paper over night. The remission ($REM^{460\ nm}$) values were measured using a Macbeth Color-Eye 7000 (CE7000), and are displayed in table 4.

Delta values ($REM^{460\ nm}_{(swatch\ washed\ with\ enzyme)}$ – $REM^{460\ nm}_{(swatch\ washed\ without\ enzyme)}$) are also indicated.

TABLE 4

Synergistic effect between hexosaminidase (SEQ ID NO 13) and DNase (SEQ ID NO 2) in deep-cleaning in model A detergent.

| Enzyme | Enzyme concentration (µg/ml) | $REM^{460\ nm}$ values | $\Delta REM^{460\ nm}$ ($REM^{460\ nm}_{with\ enzyme}$ – $REM^{460\ nm}_{without\ enzyme}$) |
|---|---|---|---|
| Sterile wfk20A swatch | 0 | 70.6 | |
| Biofilm swatch, no enzyme | 0 | 42.6 | |
| Biofilm swatch, hexosaminidase (SEQ ID NO 13) | 0.2 | 45.0 | 2.4 |
| Biofilm swatch, DNase (SEQ ID NO 2) | 0.2 | 45.2 | 2.6 |
| Biofilm swatch, hexosaminidase (SEQ ID NO 13) + DNase (SEQ ID NO 2) | 0.2 + 0.2 | 55.0 | 12.3 |

As seen in table 4, an enzyme cocktail comprising hexosaminidase (SEQ ID NO 13) and DNase (SEQ ID NO 2) provides superior deep-cleaning properties in model A detergent as compared to the individual enzymes. Given that the wash performance of the enzyme cocktail (ΔREM$^{460\ nm}$ (cocktail)=12.3) clearly exceeds the sum of the performances seen for the individual enzymes (ΔREM$^{460\ nm}$ (sum of individual enzyme treatments)=5.0), this shows a significant synergetic effect between the two enzymes on the deep-cleaning properties in model A.

The invention claimed is:

1. A method for laundering a textile, comprising:
   a. exposing a textile to a wash liquor comprising an enzyme having DNase activity and an enzyme having hexosaminidase activity, wherein the enzyme having hexosaminidase activity has at least 80% sequence identity to SEQ ID NO: 19 or at least 85% sequence identity to SEQ ID NO: 20; and
   b. completing at least one wash cycle.

2. The method of claim 1, wherein the enzyme having hexosaminidase activity has at least 85% sequence identity to SEQ ID NO: 19.

3. The method of claim 1, wherein the enzyme having hexosaminidase activity has at least 90% sequence identity to SEQ ID NO: 19.

4. The method of claim 1, wherein the enzyme having hexosaminidase activity has at least 90% sequence identity to SEQ ID NO: 20.

5. The method of claim 1, wherein the enzyme having hexosaminidase activity has at least 95% sequence identity to SEQ ID NO: 19.

6. The method of claim 1, wherein the enzyme having hexosaminidase activity has at least 95% sequence identity to SEQ ID NO: 20.

7. The method of claim 1, wherein the enzyme having hexosaminidase activity comprises SEQ ID NO: 19.

8. The method of claim 1, wherein the enzyme having hexosaminidase activity comprises SEQ ID NO: 20.

9. The method of claim 1, wherein the enzyme having DNase activity has at least 80% sequence identity to SEQ ID NO: 2.

10. The method of claim 1, further comprising rinsing the textile.

11. The method of claim 1, wherein the pH of the wash liquor is in the range 5.5 to 11.

12. The method of claim 1, wherein the temperature of the wash liquor is from about 20° C. to about 40° C.

13. The method of claim 1, wherein the textile is pre-treated with an enzyme having DNase activity and an enzyme having hexosaminidase activity.

14. The method of claim 1, wherein the concentration of DNase in the wash liquor is at least 0.00001 mg/L of enzyme per liter of wash liquor.

15. The method of claim 1, wherein the concentration of the polypeptide having hexosaminidase activity in the wash liquor is at least 0.00001 mg/L of enzyme per liter of wash liquor.

* * * * *